United States Patent [19]

Snell

[11] Patent Number: 5,716,384
[45] Date of Patent: Feb. 10, 1998

[54] METHOD AND SYSTEM FOR ORGANIZING, VIEWING AND MANIPULATING INFORMATION IN IMPLANTABLE DEVICE PROGRAMMER

[75] Inventor: Jeffery D. Snell, Oak Park, Calif.

[73] Assignee: Pacesetter, Inc., Sylmar, Calif.

[21] Appl. No.: 676,770

[22] Filed: Jul. 8, 1996

[51] Int. Cl.$^6$ .............................. A61N 1/37; A61N 1/362
[52] U.S. Cl. ........................................ 607/30; 607/32
[58] Field of Search .......................... 607/30, 31, 32, 607/59, 60

[56] References Cited

U.S. PATENT DOCUMENTS

| | | | |
|---|---|---|---|
| 4,601,291 | 7/1986 | Boute et al. | 607/27 |
| 4,809,697 | 3/1989 | Causey, III et al. | 607/31 |
| 5,292,341 | 3/1994 | Snell | 607/30 |
| 5,372,607 | 12/1994 | Stone et al. | |
| 5,447,164 | 9/1995 | Shaya et al. | 128/710 |
| 5,549,654 | 8/1996 | Powell | 607/32 |

Primary Examiner—William E. Kamm
Assistant Examiner—Carl H. Layno

[57] ABSTRACT

A method and system are provided for organizing, viewing and manipulating information in an implantable device programmer. The information includes programmable parameters which are divided into key parameters and subordinate parameters. Each key parameter has one or more associated subordinate parameters which are displayed when the user selects the key parameter, but which are not displayed when a different key parameter is selected. Subordinate parameters can be made sticky by the user. A sticky subordinate parameter is displayed regardless of whether or not the user has selected its associated key parameter. Certain parameters are linked so that when the user selects any one of the linked parameters, all linked parameters are displayed. Certain parameters are designated as inactive because of interactions with other parameters.

25 Claims, 19 Drawing Sheets

FIG. 9

John L. Smith
2022 Synchrony II 14209

- MODE..................................................DDT(DDI)
- RATE: Base..........................................70      ppm
- AV DELAY............................................188     msec
- UPPER TRACKING: Rate......................165     ppm
- SENSOR: Maximum Rate.....................140     ppm
- 360 ○ VENTRICULAR: Amplitude..............4.5     volts
- 446 — Pulse Width.....................................0.4     msec
- 448 — Pace Lead Configuration..............Bipolar
- 450 — Lead Supervision.............................On
- 452 — Sensitivity.........................................2.0     mvolt
- 454 — Sense Lead Configuration............Bipolar
- 456 — Refractory........................................275    msec
- 458 — Blanking...........................................12     msec
- 460 — Safety Standby................................On
- ATRIAL: Amplitude..............................Auto (3.75)   Volts
- PMT: Termination Options..................Off
- MAGNET: Response Mode...................Off ▶ Atrial Capture Test Batch:

Telemetry:

104

John L. Smith
2022 Synchrony II 14209

⟨M⟩
⟨A⟩
⟨V⟩
⟨E⟩

Programmer/Analyzer | Technical Manual | Patient Registration | Inventory/Sales Admin. | Set Up

| | |
|---|---|
| ● MODE..................................................DDT(DDI) | |
| 320 ○ RATE: Base...........................................60 # | ppm |
| Rate Hysteresis Search...........................On | |
| Sleep Mode Rate....................................45 | ppm |
| Antibradycardia Vasovagal Rate.............65 | ppm |
| Response Rate Delta..............................15 | ppm |
| Vasovagal Recovery Time......................12 | min |
| 330 ● AV DELAY............................................188 # | msec |
| ● UPPER TRACKING: Rate.....................165 | ppm |
| ● SENSOR: Maximum Rate.....................140 | ppm |
| ● VENTRICULAR: Amplitude...................4.5 | volt |
| 456 ⌒ Refractory.............................................275 # | msec |
| ● ATRIAL: Amplitude.............................Auto(3.75) | volts |
| 472 ⌒ PVARP.................................................125 # | msec |
| ● PMT: Termination Options....................Off | |
| ● MAGNET: Response Mode...................Off | |

204

▶ Atrial Capture Test

Batch:

Telemetry:

John L. Smith
2022 Synchrony II 14209

310
- MODE..................................................DVI
- RATE: Base........................................60 ppm
- AV DELAY.........................................100 msec
- UPPER TRACKING: Rate....................145 ppm
- SENSOR: Maximum Rate..................150 ppm
- VENTRICULAR: Amplitude................3.5 volts
○ ATRIAL: Amplitude...........................2.5 volts
   Pulse Width...................................0.3 msec
   Pace Lead Configuration...........Bipolar
   Lead Supervision........................Off
468 — Sensitivity......................................1.5 mvolt
470 — Sense Lead Configuration........Bipolar(tip)
472 — PVARP..........................................125 MSEC
○ PMT: Termination Options..............Off
390 ● MAGNET: Response Mode...............Off

204

▶ Atrial Capture Test

Batch:

Telemetry:

Programmer/Analyzer / Technical Manual / Patient Registration / Inventory/Sales Admin. / Set Up

FIG. 19

METHOD AND SYSTEM FOR ORGANIZING, VIEWING AND MANIPULATING INFORMATION IN IMPLANTABLE DEVICE PROGRAMMER

BACKGROUND OF THE INVENTION

This invention relates to analyzer-programmers that are used to interface with implantable medical devices such as implantable cardiac pacemakers and implantable cardiac defibrillators, as well as implantable cardioverters and cardioverter-defibrillators. More particularly, this invention relates to a method and system for organizing, viewing and manipulating information displayed on the display screen of an analyzer-programmer.

Implantable cardiac stimulating devices which provide therapy in response to a variety of pathological cardiac arrhythmias are known. Some implantable cardiac stimulating devices are capable of detecting pathological cardiac arrhythmias, and responding to the detected arrhythmias by providing therapeutic electrical stimulation. Some of these devices are capable of providing "tiered therapy," in which the type of electrical stimulation supplied by the device is determined in accordance with the severity of the arrhythmias, with more aggressive therapy being applied in response to more severe arrhythmias. For example, bradycardia pacing pulses may be supplied by the implantable cardiac stimulating device if the device determines that the patient's heartbeat is too slow. Antitachycardia pacing pulses may be administered if the device detects a rapid heartbeat. Higher energy cardioversion or defibrillation shocks may be provided by the device if it detects tachycardia or fibrillation.

As the patient's heart beats, the implantable cardiac stimulating device makes decisions as to whether electrical stimulation is necessary and what type of electrical stimulation to apply. This decision requires analysis of medical data gathered by the device in real-time and compared against standards stored in the implantable cardiac stimulating device. This comparison is performed by a computer program executing within the implantable cardiac stimulating device.

The computer program carries out orders given by the patient's physician. These orders are tailored by the physician for a particular patient based upon the physician's training and experience. Thus, the computer program is not an unalterable set of instructions burned into the implantable cardiac stimulating device at the time of manufacture. Instead, the program operates in a manner that is deemed to be suitable by the physician for the particular patient.

Many implantable cardiac stimulating devices serve the patient for years. During these years of service, significant changes may occur. These include changes in characteristics of the patient's health problem, changes in the characteristics of the tissue adjacent to the implantable cardiac stimulating device, changes in the characteristics of the implantable cardiac stimulating device such as remaining strength of the implanted battery, and changes in medical knowledge about cardiac arrhythmias and the preferred therapies for such arrhythmias.

Typically, a specialized computer called an analyzer-programmer communicates telemetrically with the implantable cardiac stimulating device and allows a physician to analyze the patient's condition, and the condition of the implantable cardiac stimulating device. The analyzer-programmer is also used by the physician to reset programmable parameters of the implantable cardiac stimulating device. The physician typically customizes the programmable parameters as part of the procedure to implant the implantable cardiac stimulating device. After the device is implanted, the physician typically monitors the performance of the patient's heart, the implantable cardiac stimulating device's recognition and characterization of the sinus rhythm, the implantable cardiac stimulating device's choice and timing of therapeutic electrical stimulation, and the reaction of the patient's heart to the therapy. The physician may then adjust the programmable parameters based on an assessment of these and other factors.

The programmable parameters of the implantable cardiac stimulating device are typically displayed on the display screen of the analyzer-programmer. The programmable parameters displayed by the analyzer-programmer may, for example, include the pulse width and amplitude of the electrical impulse to be applied by the implantable cardiac stimulating device to the patient's heart. Other examples of programmable parameters that are typically displayed include the lead configuration and sensitivity of sensors used by the implantable cardiac stimulating device to detect electrical signals generated by the patient's heart. The physician typically adjusts the displayed parameters so that the implantable cardiac stimulating device provides the patient's heart with appropriate electrical stimulation in view of the patient's particular circumstances.

An example of a graphical user interface for use with an analyzer-programmer is shown in commonly-assigned copending U.S. patent application Ser. No. 08/510,367, filed Aug. 2, 1995, entitled "Improved User Interface for an Implantable Medical Device Using an Integrated Digitizer Display Screen" ("the '367 application"), which is hereby incorporated by reference in its entirety. The '367 application describes a tablet computer and a digitizer pen which provides an easy to use and flexible programming system for physicians. To select a programmable parameter, the physician simply touches a displayed parameter with the digitizer pen. This frees the physician from the often cumbersome process of selecting programmable parameters via a keyboard. Freedom from the inconveniences of using a keyboard is particularly useful during the procedure to implant the device, when physicians and medical assistants are busy attending the patient.

Another system for displaying and modifying programming information is described in U.S. Pat. No. 4,809,697 ("the '697 patent"). The '697 patent describes a system which implements a touchscreen to allow the user to navigate from screen to screen and make changes by touching certain regions of the display screen.

The complexity and functionality of implantable cardiac stimulating devices has rapidly increased with the advent of the use of programmable microprocessors within these devices. The increased sophistication of implantable cardiac stimulating devices has, in turn, lead to a dramatic increase in the number of programmable parameters. In 1979, for example, the typical implantable cardiac stimulating device had 6 programmable parameters with an average of 6 possible values for each parameter. In 1993, a typical device had 28 parameters with an average of 8 possible values for each parameter. In the near future, a device may have as many as 40 parameters with 16 possible values for each parameter.

Physicians working with new implantable cardiac stimulating devices often suffer from information overload when working with such a large number of parameters. When making adjustments to the electrical stimulation provided by the implantable cardiac stimulating device, the physician is often faced with the very difficult task of considering and adjusting a large number parameters. With so many parameters displayed on the display screen, the physician may have difficultly focusing on the particular parameters which may be important at a particular time.

Displaying 40 parameters with 16 values for each parameter on the screen of an analyzer-programmer using conventional methods requires multiple screens or multiple windows. Conventional methods, however, suffer from the drawback of requiring the physician to resort to the cumbersome process of switching between several screens to view all of the parameters.

It would be desirable if all information relevant to a particular analysis or procedure could be displayed on one screen. In fact, it is often the case that only a subset of all programmable parameters is applicable to the particular analysis or procedure being performed. However, conventional analyzer-programmers do not organize information in a manner that facilitates such grouping of information.

SUMMARY OF THE INVENTION

To address the problem of viewing and adjusting a large number of programmable parameters, the present invention preferably provides an analyzer-programmer which organizes the programmable parameters into a hierarchical structure and provides rules for interactively displaying portions of the structure to the physician. The system preferably allows the physician to view certain parameters while others remain hidden from view. Preferably, only those parameters which are important to the particular procedure that the patient is undergoing are displayed. This reduces the amount of information displayed on the screen so that the physician may focus on the information that is important to the task at hand. The present invention also allows the physician to select which parameters are displayed so that the physician can tailor the display to fit the current procedure.

In a preferred embodiment, the present invention provides a two-level cognitive hierarchy of programmable parameters and defines a set of rules by which the parameters are shown to or hidden from the physician. A preferred embodiment of a two-level cognitive hierarchy is made by dividing the programmable parameters into two groups—key parameters and subordinate parameters. The key parameters preferably include the most important parameters. For example, in a preferred embodiment for a dual-chamber pacemaker, the key parameters may include pacing mode, base rate, AV delay, upper tracking rate, maximum sensor rate, ventricular pulse amplitude, atrial pulse amplitude, PMT termination options, and magnet response mode. Each of the remaining parameters is then defined as subordinate to at least one of the key parameters. In other words, each subordinate parameter is associated with at least one of the key parameters.

The key parameters and subordinate parameters preferably are displayed according to the following rules. In a preferred embodiment only the key parameters are initially displayed so as to provide a convenient summary of the state of the implantable cardiac stimulating device. In another preferred embodiment, the key parameters and the subordinate parameters of a default key parameter are initially displayed.

When the physician selects one of the key parameters, the parameters subordinate to the selected key parameter preferably are displayed. In a preferred embodiment, the parameters subordinate to the ventricular pulse amplitude consist of the following—pulse width, pace lead configuration, lead supervision, sensitivity, sense lead configuration, refractory period, blanking period, and safety standby status. When the physician selects the ventricular pulse amplitude parameter, these subordinate parameters preferably are displayed.

When a different key parameter is selected, the subordinate parameters for the originally selected key parameter preferably are hidden, while those of the new key parameter preferably are displayed.

The subordinate programmable parameters preferably can be made "sticky" by the physician. A sticky subordinate parameter preferably remains displayed even if a different key parameter is selected. Using the example of a dual-chamber pacemaker again, the ventricular refractory period, which preferably is subordinate to the ventricular amplitude, may be adjusted by the physician from 275 milliseconds to 225 milliseconds for example. Once it has been adjusted, the ventricular refractory period will continue to be displayed, even if another key parameter is selected. In a preferred embodiment, the physician or other user is able to make a parameter sticky by designating it for programming without actually changing its value.

Certain parameters preferably are linked so that if one of the linked parameters becomes sticky, then the other linked parameters also become sticky. Once a parameter is selected for programming, all other parameters linked to that parameter preferably are displayed, regardless of which key parameter is currently selected by the physician.

In a preferred embodiment, programmable parameters can become inactive due to the status of other parameters. Since it may often be valuable to know the setting of the inactive parameters, and also be aware that they are presently inactive, inactive parameters preferably are displayed in a manner different than that used for the active parameters. The inactive parameters can, for example, be shown in grey rather than black.

The present invention reduces or eliminates the information overload experienced by the physician by reducing the total number of parameters viewed at any time. The present invention also allows the physician to quickly and easily view any parameter. In addition, by permitting the physician to designate sticky parameters, the present invention allows the physician to adapt the display to show those parameters which are of immediate interest. The physician is thus able to tailor the display so that he or she can focus on the parameters that are relevant to the current procedure.

BRIEF DESCRIPTION OF THE DRAWINGS

The above and other advantages of the present invention will be apparent upon consideration of the following detailed description, taken in conjunction with the accompanying drawings, in which like reference characters refer to like parts throughout, and in which:

FIG. 9 is an illustrative screen display of the analyzer-programmer when the user has selected the ventricular amplitude parameter in accordance with the present invention;

FIG. 18 is an illustrative screen display of the analyzer-programmer when the user has adjusted the value of the base rate parameter and caused linked parameters to be displayed in accordance with the present invention;

FIG. 19 is an illustrative screen display showing the display of inactive parameters in accordance with the present invention.

DETAILED DESCRIPTION OF THE PREFERRED EMBODIMENTS

The present invention can preferably be used with analyzer-programmer computers which use a digitizer pen, conventional keyboard, light pen, touch screen or any other technique to allow the user to input information. A preferred embodiment of the present invention uses a portable tablet computer having a digitizer pen. A preferred example of a tablet computer is described in the above-incorporated '367 patent application, and is briefly described hereinbelow.

The term "user" as used herein includes physicians, medical specialists, medical assistants, and any other appropriate persons using the tablet computer to adjust or select programmable parameters displayed on the display screen of the tablet computer. The present invention is in no way limited to use by physicians.

Figure 1:
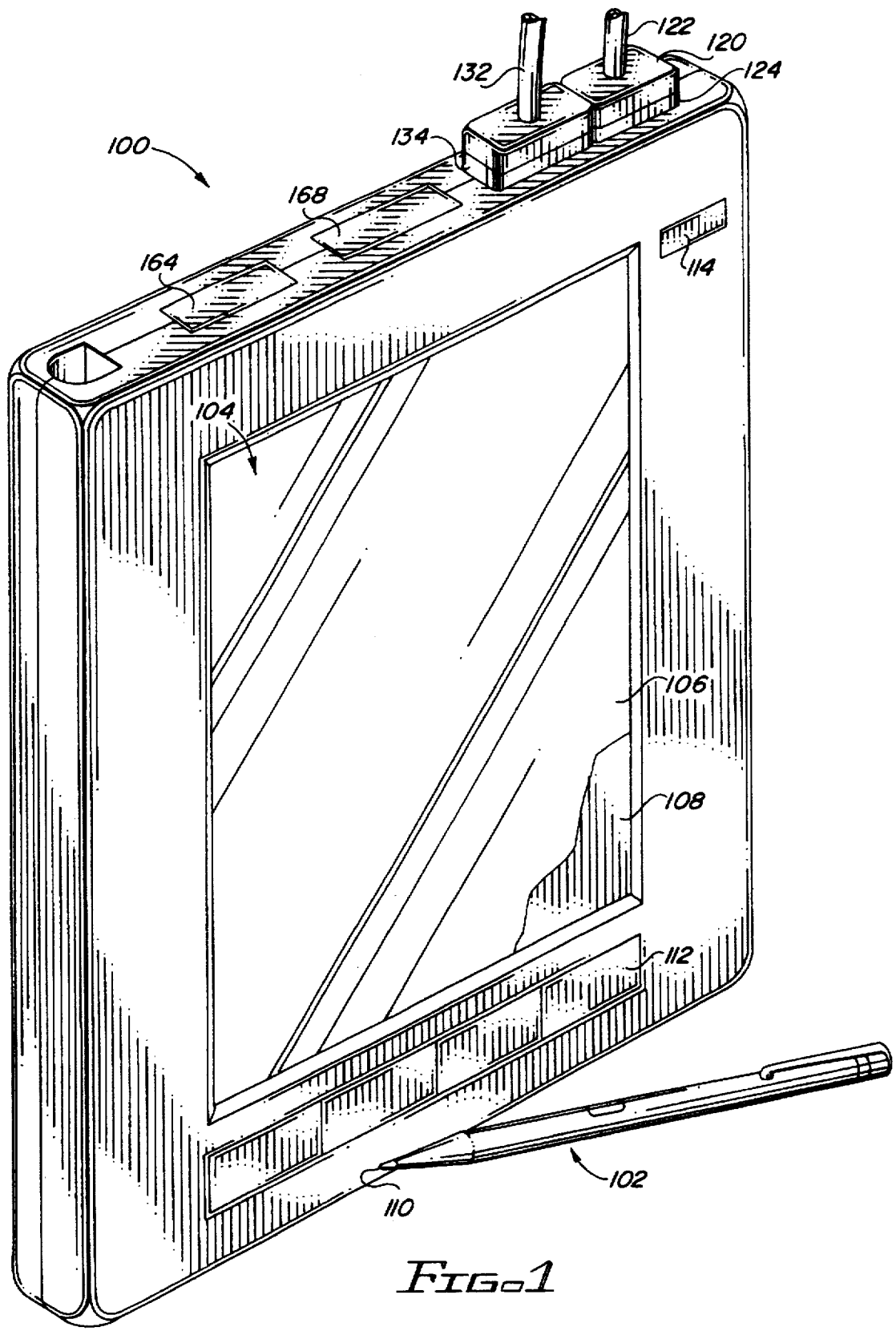
FIG. 1 is a perspective view of a tablet computer which can be used to implement the present invention.

In FIG. 1, a tablet computer 100, and a digitizer pen 102 for inputting information are shown along with components of the tablet computer. The pen 102 can be used to select among presented choices on a digitizer display screen 104. The digitizer display screen 104 is comprised of a display 106 and a digitizer 108 which overlap one another. The user selects an item (not shown) by touching a pen tip 110 to the display screen 104.

Emergency keys 112 preferably are provided on the tablet computer 100. The emergency keys 112 provide the physician or medical specialist with several important functions for controlling the tablet computer 100 during an emergency.

The tablet computer 100 is turned on and off with an on/off switch 114.

Figure 2:
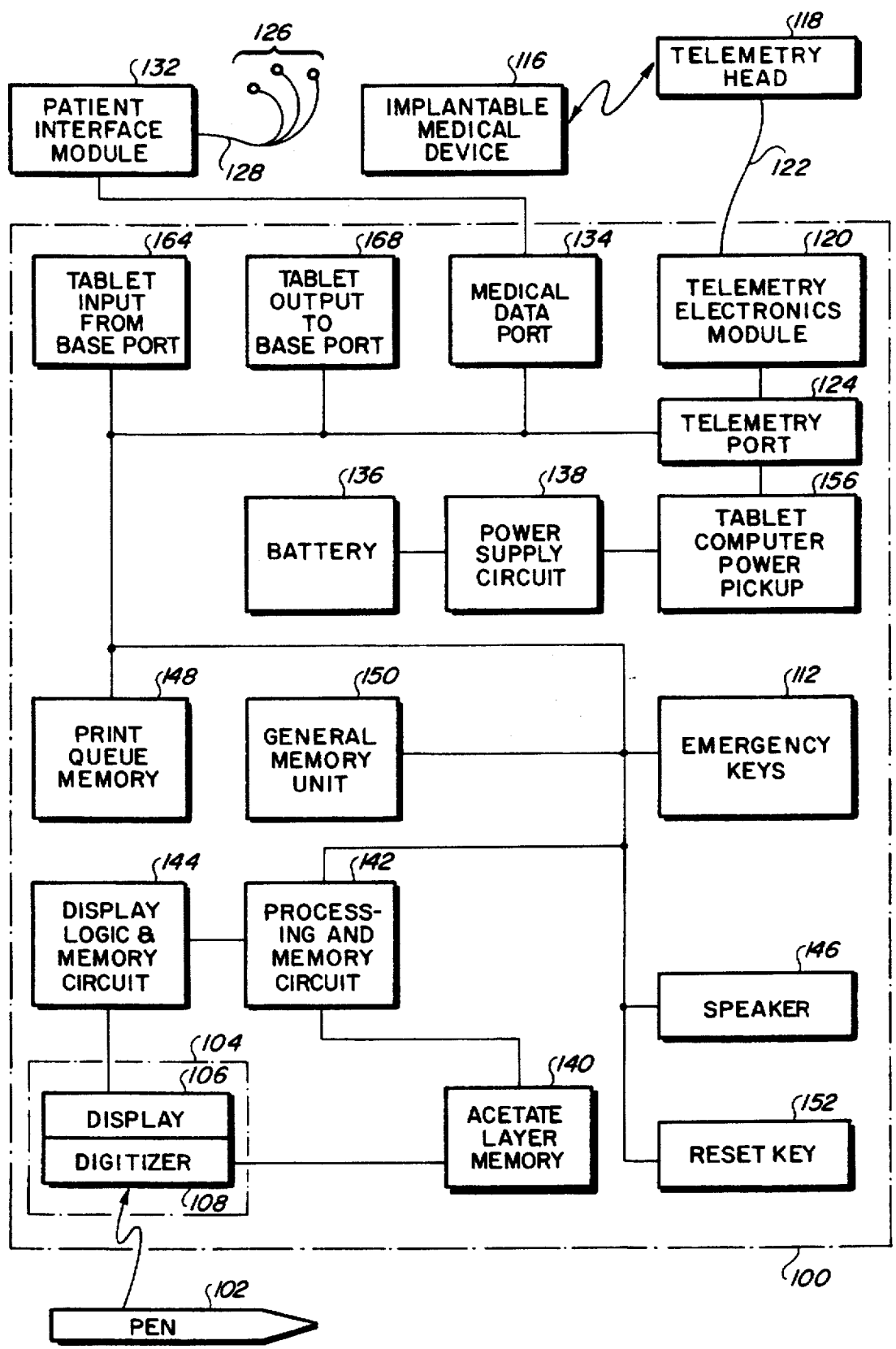
FIG. 2 is a block diagram of the tablet computer of FIG. 1 showing functional elements and showing the sources of input.

Referring now to FIG. 2, an implantable cardiac stimulating device 116 can sense cardiac activity and provide therapeutic electric stimulation through electrical leads (not shown). The information received by the implantable cardiac stimulating device 116 include IEGM waveforms from the atrial and ventricular regions of the heart, and marker data channel information generated within the implantable cardiac stimulating device 116. Marker data channel information contains a record of discrete acts of the implantable cardiac stimulating device 116 such as the application of a therapeutic electric pulse, and also the recognition by the implantable cardiac stimulating device 116 of certain heart activities as sensed by the implantable cardiac stimulating device 116.

A telemetry head 118 is attached to a telemetry electronics module 120 by a telemetry cable 122. The telemetry electronics module 120 is plugged into a telemetry port 124. (Note that the connection of the telemetry cable 122 into the telemetry electronics module 120 and the telemetry port 124 is also shown in FIG. 1.) The telemetry electronics module 120 performs conversions of the telemetry data such as a conversion from analog data to digital data if the implantable cardiac stimulating device 116 does not itself perform the analog-to-digital conversion. The tablet computer 100 preferably uses the same cable and port for telemetry data transmitted in either direction between the tablet computer 100 and the implantable cardiac stimulating device 116.

In addition to data collected by the implantable cardiac stimulating device 116, medical data can be collected from surface ECG leads 126. The surface ECG leads 126 are placed on the skin of the patient (not shown). A surface ECG cable 128 has a number of strands that preferably can be attached and detached to the surface ECG leads 126. The surface ECG leads 126 are connected via the surface ECG cable 128 to a patient interface module 130 which performs conversion of the surface ECG waveform into digital format and performs other processing of the waveform data. The patient interface module 130 is connected to the tablet computer 100 by a medical data port cable 132 at a medical data port 134. (Note that the connection of the medical data port cable 132 to the medical data port 134 is also shown in FIG. 1.)

The tablet computer 100 is provided with energy during mobile operation by a battery 136 connected to a power supply circuit 138. The digitizer display screen 104 is shown in FIG. 2 in its constituent parts—the digitizer 108 and the display 106. The input from the pen 102 is received by the digitizer 108 and placed in an acetate layer memory 140 where the input is processed in a processing and memory circuit 142. A display logic and memory circuit 144, which communicates with the processing and memory circuit 142, controls the display 106.

A speaker 146 is used within the tablet computer 100 to provide audio alarms in response to detected problems concerning the patient's heart, the monitoring equipment, the input from the physician or medical specialist, or other problems. The speaker 146 can also be used to confirm the receipt of input.

The tablet computer 100 contains a print queue memory 148 which stores requests to create a printout until the tablet computer 100 is connected directly or indirectly to a printer (described below in connection with FIG. 3). The print queue memory 148 is non-volatile memory and preferably is a memory card.

In addition to the acetate layer memory 140, the memory in the processing and memory circuit 142, the memory in the display logic and memory circuit 144, and the non-volatile memory in the print queue memory 148, the tablet computer 100 has a general memory unit 150. The general memory unit 150 may, for example, be used to store patient data and reference material available to the physician or medical specialist such as a dictionary, phone directory, medical reference text, or reference manuals on implantable medical controllers. A conventional hard drive is preferably used for the general memory unit 150.

In addition to the emergency keys 112, a reset key 152 is preferably provided to re-initialize the tablet computer 100. In alternative embodiments of the tablet computer 100, the reset key could be one of the emergency keys 112.

Figure 3:
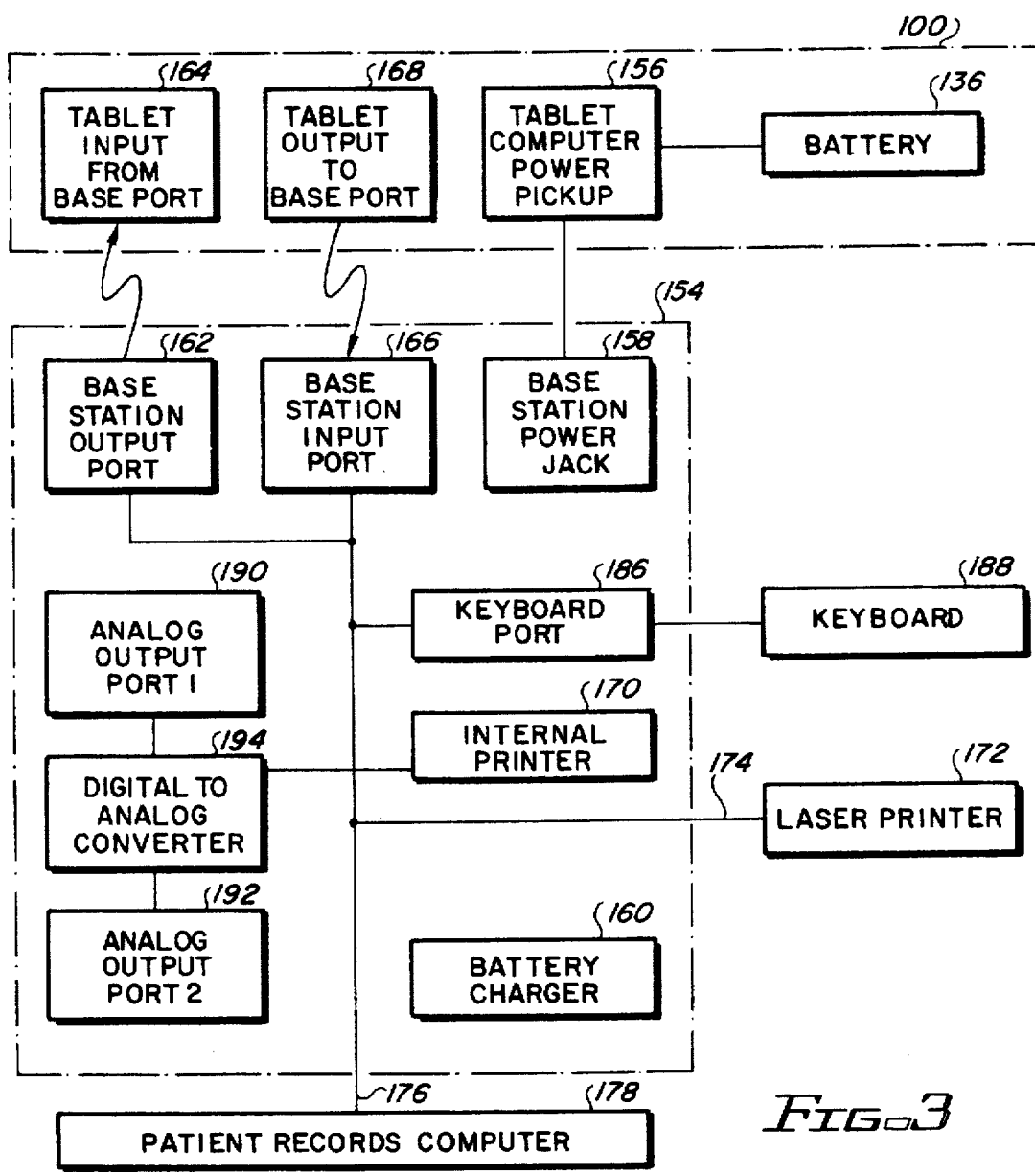
FIG. 3 is a block diagram of the tablet computer of FIGS. 1 and 2, showing the tablet computer connected to a base station, the base station being further connected to a patient records computer and to peripheral devices.

Referring now to FIG. 3, the tablet computer 100 is periodically inserted into a base station 154. A tablet computer power pickup 156 mates with a base station power jack 158 during the insertion of the tablet computer 100 into the base station 154 to provide a source of power to the tablet computer 100. A battery charger 160 is contained in the base station 154 for charging batteries 136 for use in the tablet computer 100.

The base station 154 and tablet computer 100 have connections that allow the tablet computer 100 to communicate with the base station 154 when inserted in the base station 154. The base station 154 preferably uses LEDs (light emitting diodes) for an infrared serial communication link between the tablet computer 100 and the base station 154. Specifically, a base station output port 162 is placed adjacent to a tablet input from base port 164 and a base station input port 166 is placed adjacent to a tablet output to base port 168. (Note that base ports 164 and 168 are also shown in FIG. 1.) These ports are preferably small windows for transmitting the infrared signals. As shown in FIG. 3, small gaps exists between the communication ports (162 to 164 and 166 to 168) as distinguished from the physical contact established between the base station power jack 158 and the tablet computer power pickup 156.

An internal printer 170 is integral to the base station 154, while a laser printer 172 is connected to the base station 154 by a laser printer connection cable 174.

The base station 154 is at least periodically connected by a base to host cable 176 to a patients' records computer 178. The patients record computer 178 stores medical data records and other information that is relevant to the use of the tablet computer 100.

An optional connection to the base station 154 is a keyboard 188, connected via a keyboard port 186, to be used by field service engineers in customizing the tablet computer 100. The keyboard 188 could also be used to enter patient data into a tablet computer 100 while the tablet computer 100 is inserted in the base station 154. Another optional attachment is a bar code reader (not shown) which could be connected to the keyboard port 186 to allow bar codes to be scanned. As an example of bar code reader use, some hospitals may position the base station 154 along with the bar code reader into the operating room to read a patient identification bar code number along with the bar code representation of each piece of equipment or material used during the implantation of the implantable cardiac stimulating device 116 (FIG. 2).

Analog output ports 190 and 192 are provided so that other devices can be connected to the base station 154. The medical data provided to the tablet computer 100 through the medical data port 134 (FIG. 2) and the telemetry port 124 (FIG. 2) can be passed through the tablet output to base port 168 to the base station input port 166 and converted into analog form in a digital-to-analog converter 194 before passing out of one of the analog output ports 190 or 192 to peripheral devices such as paper chart recorders (not shown), large video monitors (not shown) for use in teaching, or calibration equipment (not shown).

Figure 4:
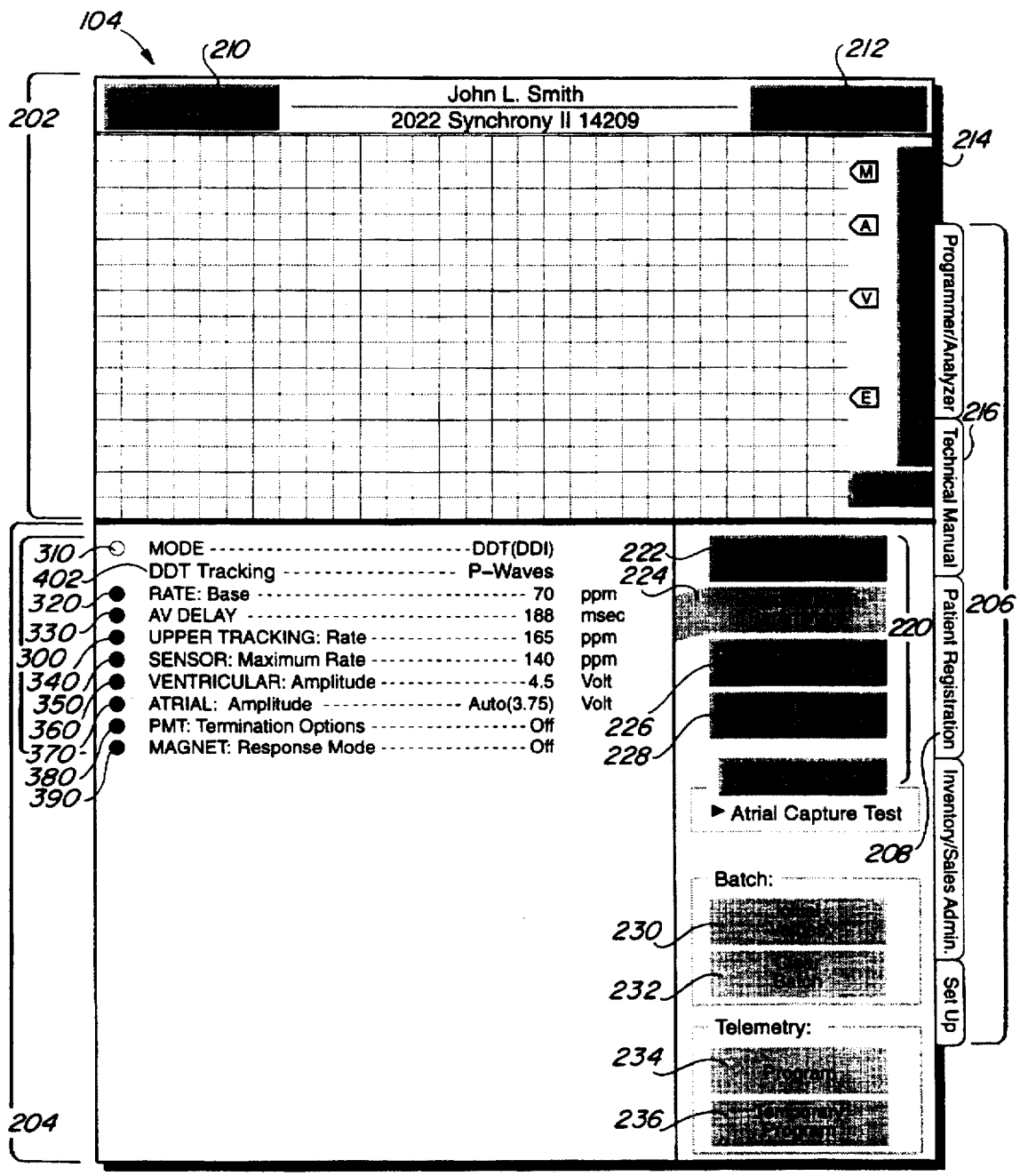
FIG. 4 is an illustrative screen display on the digitizer display screen of the tablet computer showing the display of programmable parameters, including key parameters, in accordance with the present invention.

Turning now to FIG. 4, a view of the digitizer display screen 104 is shown. The tablet computer 100 (FIG. 1) responds when the pen 102 (FIG. 1) taps one of the regions on the digitizer display screen 104 that is a current trigger for action by the tablet computer 100 (FIG. 1). The size, location, and number of regions that act as triggers are controlled by the tablet computer 100 (FIG. 1) and change during the use of the tablet computer 100 (FIG. 1). These regions are called buttons.

The digitizer display screen 104 appears to be one component to the physician or medical specialist, but as described in connection with FIGS. 1 and 2 is actually two distinct components. The buttons exist on the digitizer 108 (FIG. 1) in the display digitizer screen 104, and unlike the input keys on a keyboard, the buttons are invisible to the physician or medical specialist. The tablet computer 100 (FIG. 1) can cause the display 106 (FIG. 1) to provide an image directly overlying the button. The image could be a box with text to indicate the effect of tapping on that button. The combination of input regions and buttons on the digitizer 108 (FIG. 1) and the corresponding image on the display 106 (FIG. 1) containing windows of data and images overlying buttons form a screen display.

The digitizer display screen 104 has an upper window 202 and a lower window 204 and vertical tabs 206. The physician or medical specialist preferably uses the vertical tabs 206 to move from one display screen to another. For example, tapping the Patient Registration button 208 will cause information about the patient to be displayed on the screen (not shown). Vertical tabs 206 are preferably made to resemble tabs on a three-ring binder in order to facilitate intuitive operation by the user.

An emergency program button 210, a display options button 212, a freeze button 214, and a show button 216 are located in upper window 202. These buttons are used to control the information displayed in the upper window 202.

The upper window 202 preferably is used to display current medical data sensed by the implantable cardiac stimulating device 116 and surface ECG leads 126 (FIG. 1). Normally, four channels of information are displayed simultaneously. The four channels are a surface ECG channel, a marker data channel, an atrial IEGM (AIEGM) channel, and a ventricular IEGM (VIEGM) channel. The display and notation this data is described in detail in the above-incorporated '367 application.

The lower window 204 has display selection buttons 220 which include a follow-up procedures button 222, a programmable parameters button 224, a system options button 226, and a print options button 228. The selected button preferably is highlighted in order to remind the physician or medical specialist the current choice for display. In this case, user selection of the programmable parameters button 224 preferably causes the programmable parameters button 224 to be highlighted. Below the display selection buttons are an initial values button 230 a clear batch button 232, a program button 234, and a temporary program button 236.

In accordance with the present invention, the programmable parameters are organized into a hierarchical structure so that some of the parameters are displayed on the display screen 104, while others remain hidden. In a preferred embodiment of the present invention shown in FIGS. 4–10, the programmable parameters are organized into a two-level cognitive hierarchy in which the programmable parameters are divided into key parameters 300 and subordinate parameters. At least some of the key parameters 300 preferably have at least one associated subordinate parameter. In a preferred embodiment of the present invention shown in FIGS. 4–10, the key parameters 300 consist of a mode parameter 310, a base rate parameter 320, an AV delay parameter 330, an upper tracking rate parameter 340, a sensor maximum rate parameter 350, a ventricular amplitude parameter 360, atrial amplitude parameter 370, a PMT termination options parameter 380, and a magnet response mode parameter 390.

FIG. 4 shows the display screen 104 after the user has selected the programmable parameters button 224. When the user selects the programmable parameters button 224, the key parameters 300 preferably are displayed to the user in the lower display window 204. In a preferred embodiment, the initial display includes the subordinate parameters of a default key parameter. As shown in FIG. 4, the mode parameter 310 preferably is the default key parameter. A DDT tracking parameter 402 preferably is subordinate to the mode parameter 310, and preferably is initially displayed along with the key parameters 300. The DDT tracking parameter 402, which is subordinate to the mode parameter 310, preferably is displayed whenever the mode parameter 310 is selected.

The user can select one or more of the programmable parameters 300 in order to display the programmable parameters which are subordinate to the selected key parameter. The user preferably selects one of the key parameters 300 by tapping the parameter on the display screen 104 with the pen 102 (FIG. 1). When the user selects one of the key parameters 300, the parameters which are subordinate to the selected key parameter preferably are displayed, while the subordinate parameters associated with the other key parameters are not displayed.

Figure 5:
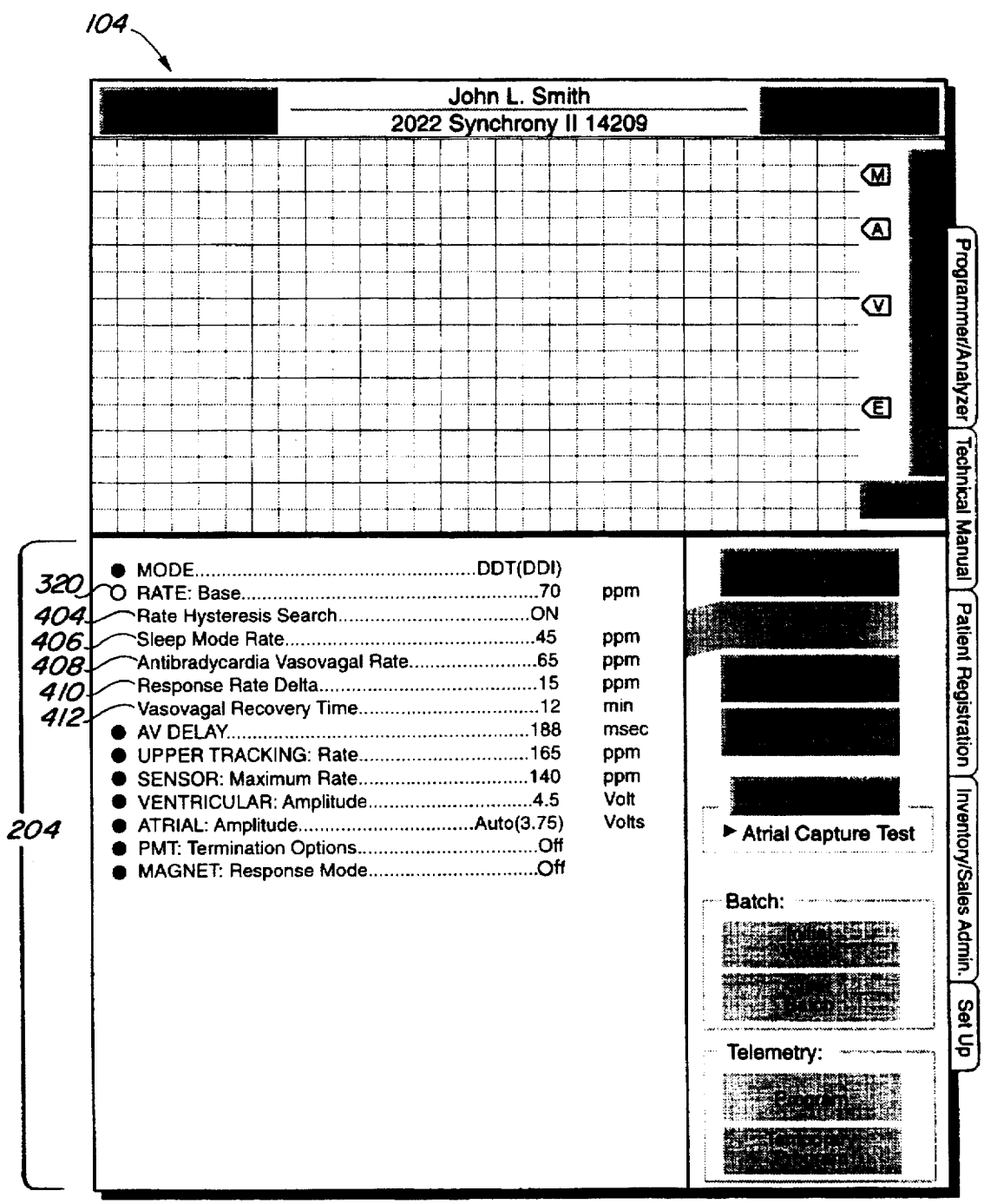
FIG. 5 is an illustrative screen display on the analyzer-programmer when the user has selected the base rate parameter in accordance with the present invention.

FIG. 5 shows the lower display window 204 when the user has selected the base rate parameter 320. The subordinate parameters of the base rate parameter 310 preferably are a rate hysteresis search parameter 404, a sleep mode rate parameter 406, an antibradycardia vasovagal rate parameter 408, a response rate delta parameter 410, and a vasovagal recovery time parameter 412. When the user selects the base rate parameter 320, subordinate parameters 404, 406, 408, 410, and 412 associated with the base rate parameter 320 preferably are displayed, while the subordinate parameters of the other key parameter preferably are not displayed.

Figure 6:
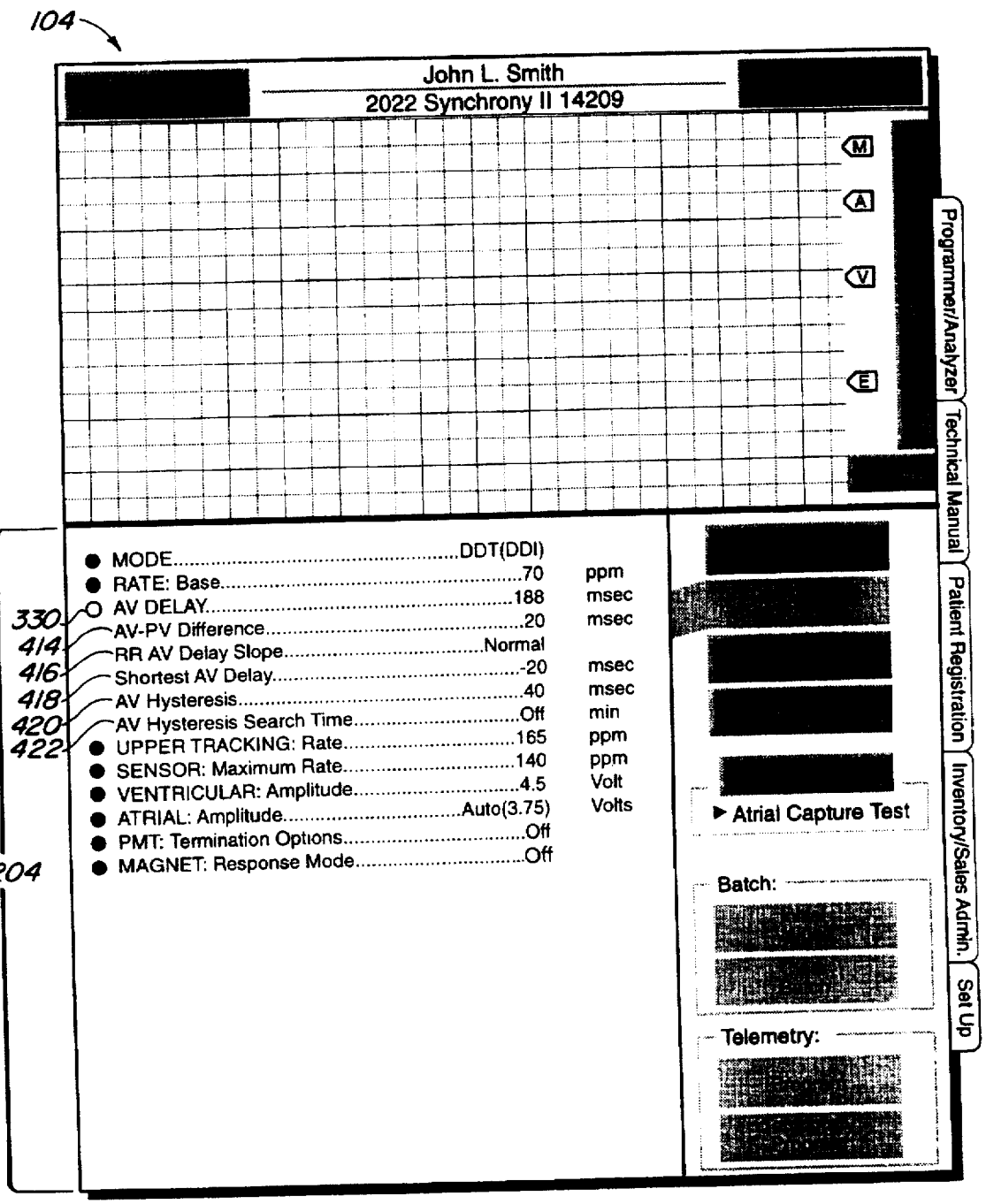
FIG. 6 is an illustrative screen display on the analyzer-programmer when the user has selected the AV delay parameter in accordance with the present invention.

FIG. 6 shows the lower display window 204 when the user has selected the AV delay parameter 330. The subordinate parameters of the AV delay parameter 330 preferably are an AV-PV difference parameter 414, a RR AV delay scope parameter 416, a shortest AV delay parameter 418, an AV hysteresis parameter 420, and an AV hysteresis search time parameter 422. When the user selects the AV delay parameter 330, subordinate parameters 414, 416, 418, 420, and 422 associated with the AV delay parameter 330 preferably are displayed, while the subordinate parameters of the other key parameters preferably are not displayed.

Figure 7:
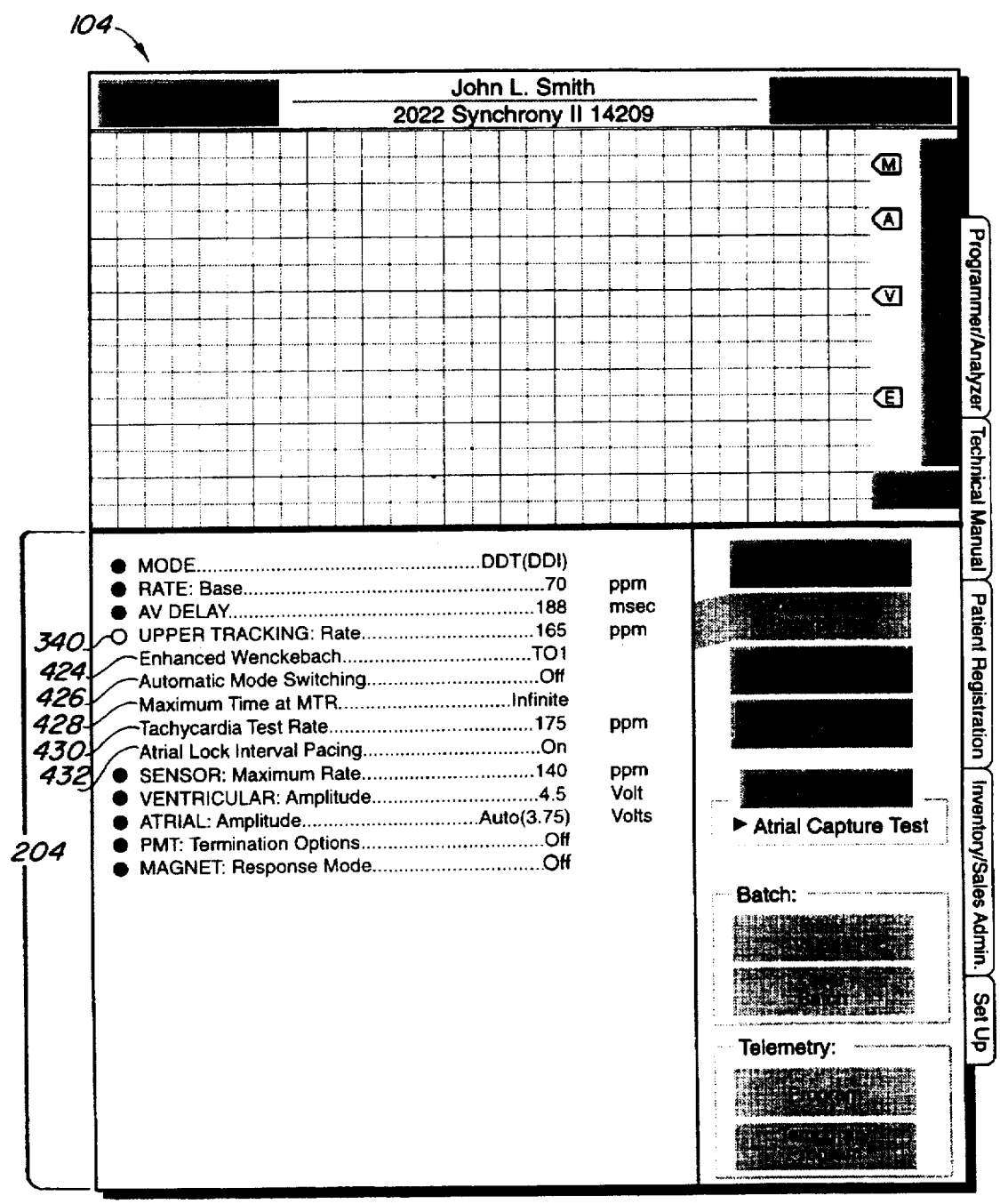
FIG. 7 is an illustrative screen display of the analyzer-programmer when the user has selected the upper tracking rate parameter in accordance with the present invention.

FIG. 7 shows the lower display window 204 when the user has selected the upper tracking rate parameter 340. The subordinate parameters of the upper tracking rate parameter 340 preferably are an enhanced Wenckebach parameter 424, an automatic mode switching parameter 426, a maximum time at MTR parameter 428, a tachycardia test rate parameter 430, and an atrial lock interval pacing parameter 432. When the user selects the upper tracking rate parameter 340, subordinate parameters 424, 426, 428, 430, and 432 associated with the upper tracking rate parameter 340 preferably are displayed, while the subordinate parameters of the other key parameters preferably are not displayed.

Figure 8:
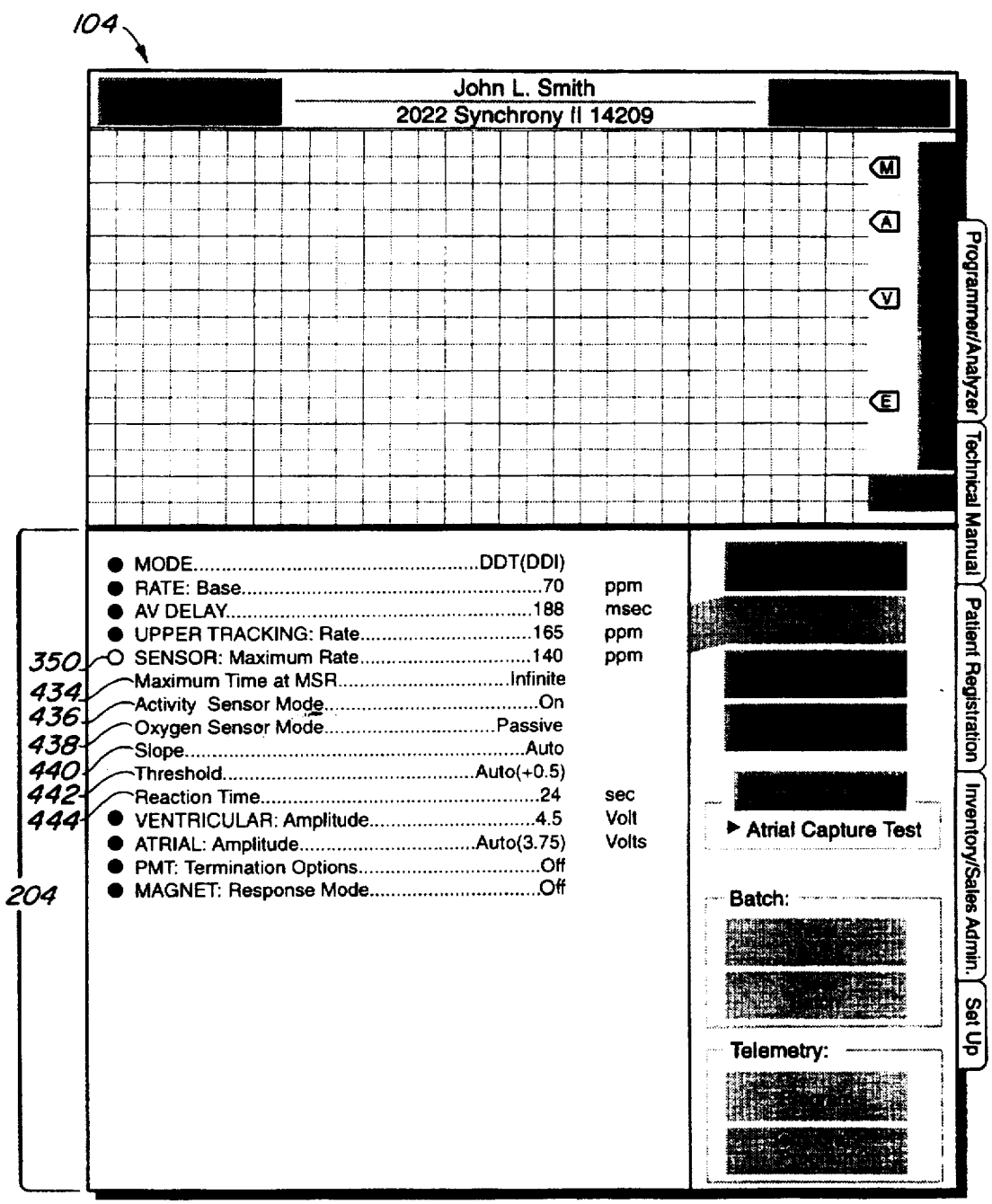
FIG. 8 is an illustrative screen display of the analyzer-programmer when the user has selected the sensor maximum rate parameter in accordance with the present invention.

FIG. 8 shows the lower display window 204 when the user has selected the sensor maximum rate parameter 350. The subordinate parameters of the sensor maximum rate parameter 350 preferably are a maximum time at MSR parameter 434, an activity sensor mode parameter 436, an oxygen sensor mode parameter 438, a slope parameter 440, a threshold parameter 442, and a reaction time parameter 444. When the user selects the sensor maximum rate parameter 350, subordinate parameters 434, 436, 438, 440, 442, and 444 associated with the sensor maximum rate parameter 350 preferably are displayed, while the subordinate parameters of the other key parameters preferably are not displayed.

FIG. 9 shows the lower display window 204 when the user has selected the ventricular amplitude parameter 360. The subordinate parameters of the ventricular amplitude parameter 360 preferably are a ventricular pulse width parameter 446, a ventricular pace lead configuration parameter 448, a ventricular lead supervision parameter 450, a ventricular sensitivity parameter 452, a ventricular sense lead configuration parameter 454, a ventricular refractory parameter 456, a ventricular blanking parameter 458, and a ventricular safety standby parameter 460. When the user selects the ventricular amplitude parameter 360, subordinate parameters 446, 448, 450, 452, 454, 456, 458, and 460 preferably are displayed, while the subordinate parameters of the other key parameters preferably are not displayed.

Figure 10:
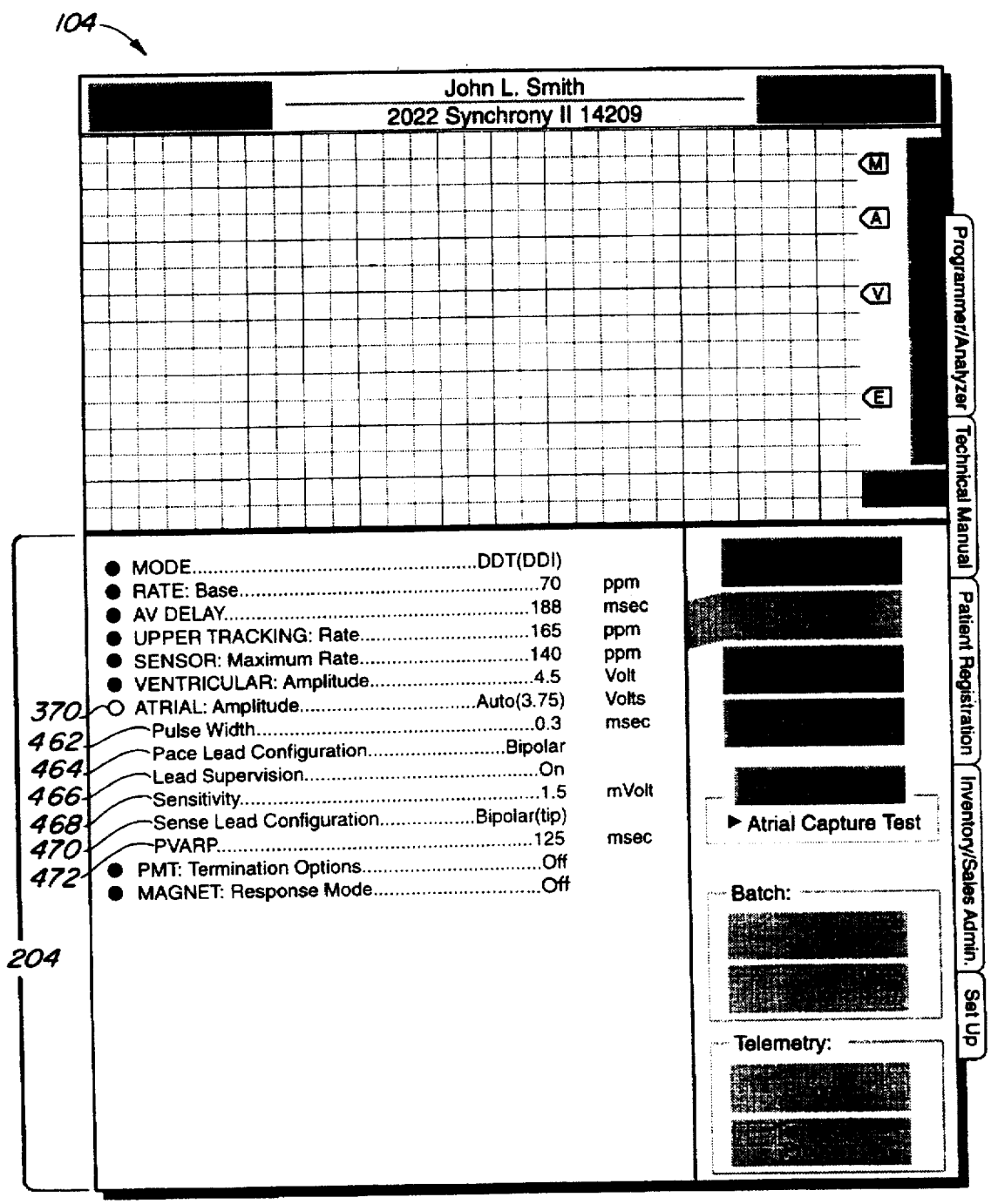
FIG. 10 is an illustrative screen display of the analyzer-programmer when the user has selected the atrial amplitude parameter in accordance with the present invention.

FIG. 10 shows the lower display window 204 when the user has selected the atrial amplitude parameter 370. The subordinate parameters of the atrial amplitude parameter 370 preferably are an atrial pulse width parameter 462, an atrial lead configuration parameter 464, an atrial lead supervision parameter 466, an atrial sensitivity parameter 468, an atrial sense lead configuration parameter 470, and a PVARP parameter 472. When the user selects the atrial amplitude parameter 370, subordinate parameters 462, 464, 466, 468, 470, and 472 preferably are displayed, while the subordinate parameters of the other key parameters preferably are not displayed.

In accordance with the present invention, some key parameters preferably do not have associated subordinate parameters. In this example, the PMT termination options parameter 380 and the magnet response mode parameter 390 do not have associated subordinate parameters.

Although FIGS. 4–10 show the selection of a single key parameter and the display of the subordinate parameters of the selected key parameter, in another embodiment of the present invention (not shown), the user can select more than one key parameter for display in lower display window 204. In this alternative embodiment, the subordinate parameters of all selected key parameters may be simultaneously shown. For example, the user could select both the ventricular amplitude and atrial amplitude key parameters, and the subordinate parameters of both of these key parameters preferably would be displayed (not shown).

In accordance with another aspect of the present invention, subordinate parameters preferably become "sticky" when they are adjusted or when the user designates them as such. A sticky subordinate parameter preferably is displayed in the lower display window 204, independent of whether or not its associated key parameter is selected by the user. By designating a subordinate parameter as sticky, the user is able to tailor the display to show those parameters which are of greatest interest to the user.

Figure 11:
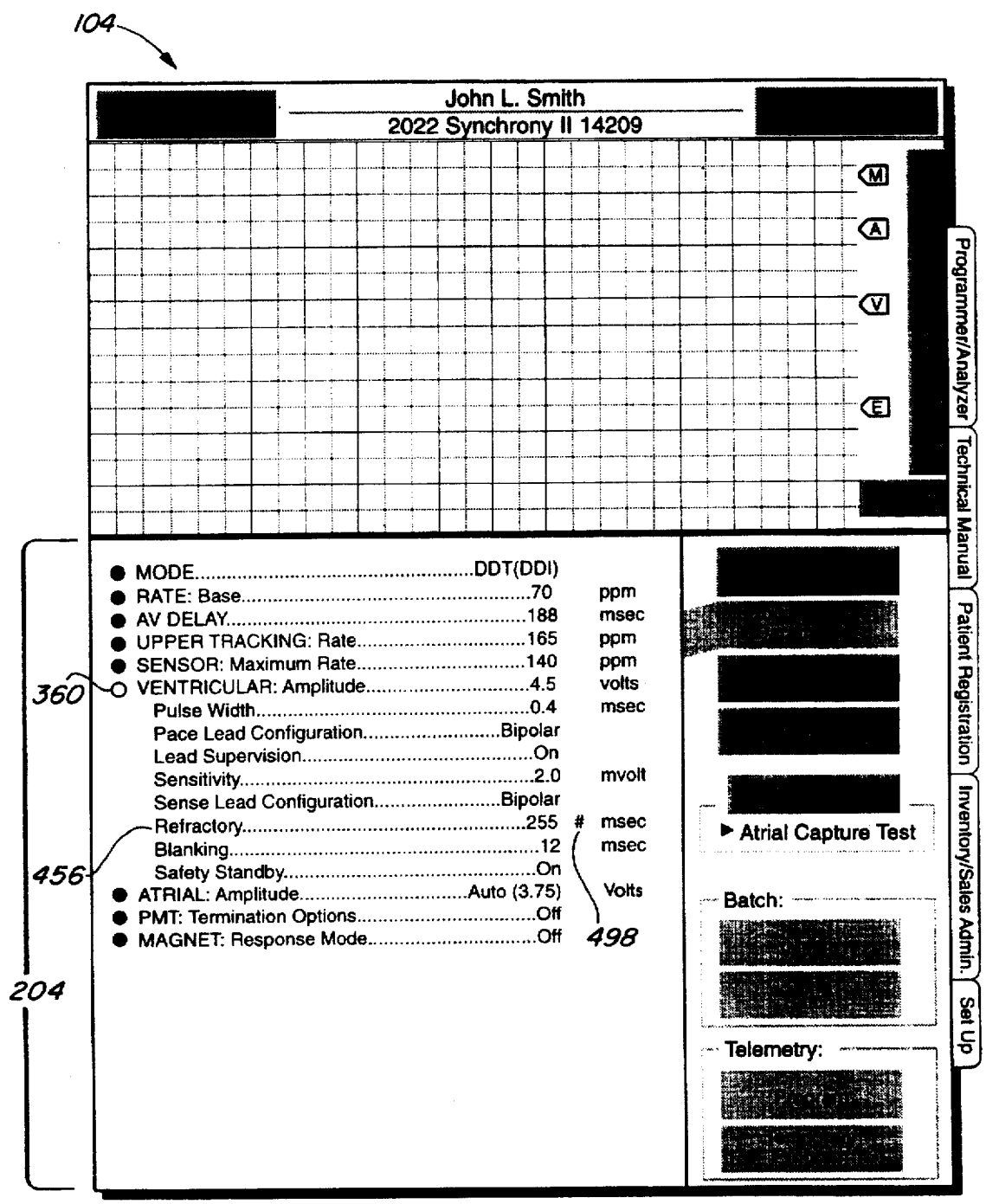
FIG. 11 is an illustrative screen display of the analyzer-programmer when the user has made the ventricular refractory period parameter sticky in accordance with the present invention.

FIGS. 11–14 show the use of sticky parameters in accordance with the present invention. FIG. 11 shows the lower display window 204 when the user has selected the ventricular amplitude parameter 360. The user has changed the value of the ventricular refractory parameter 456 to 225 milliseconds from the original value of 275 milliseconds shown in FIG. 9. Adjusting the value of the ventricular refractory parameter 456 causes the refractory parameter 456 to become sticky. Sticky parameters preferably can be indicated as such on the display screen 104 by displaying a "#" mark next to the sticky parameter as shown by a mark 498 in FIG. 11.

Numerous techniques can be used to allow the user to adjust the value of a parameter. The above-incorporated '367 application describes the use of a pop-up window which allows the user to chose a new value for a programmable parameter. Other techniques can also be used. For example, after selecting a parameter, the user could change its value via a conventional keyboard. In general, any known technique can be used with the present invention to allow the user to change the value of a programmable parameter.

Changes made to the programmable parameters preferably are stored within the tablet computer 100 (FIG. 1) until the physician or medical specialist sends all of the changes to the implantable cardiac stimulating device 116 (FIG. 2) via the telemetry. This is known as batch programming.

Figure 12:
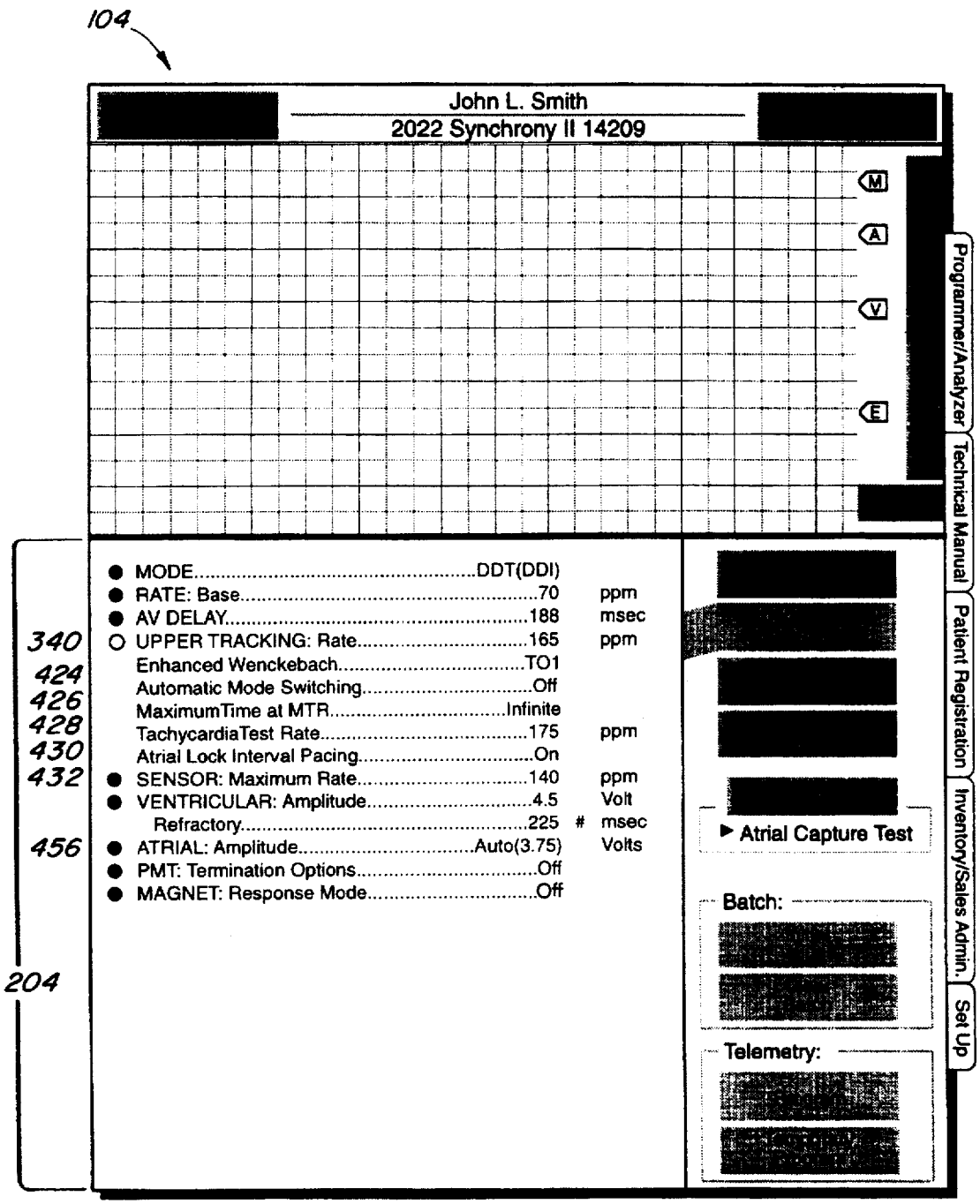
FIG. 12 is an illustrative screen display of the analyzer-programmer when the user has selected the upper tracking rate parameter, the screen display including the sticky parameter in accordance with the present invention.

FIG. 12 shows the display screen 104 when the user has selected the upper tracking rate parameter 340. By previously adjusting the value of the ventricular refractory period, the user caused the ventricular refractory period parameter 456 to become sticky. The ventricular refractory parameter 456 is thus displayed in addition to the subordinate parameters 424, 426, 428, 430, and 432 of the upper tracking rate parameter 340, even though the ventricular refractory parameter 456 is not subordinate to the selected upper tracking rate parameter 340. The subordinate parameters 446, 448, 450, 452, 454, and 458 of the ventricular amplitude parameter 360 which were not adjusted by the user preferably are not displayed.

Figure 13:
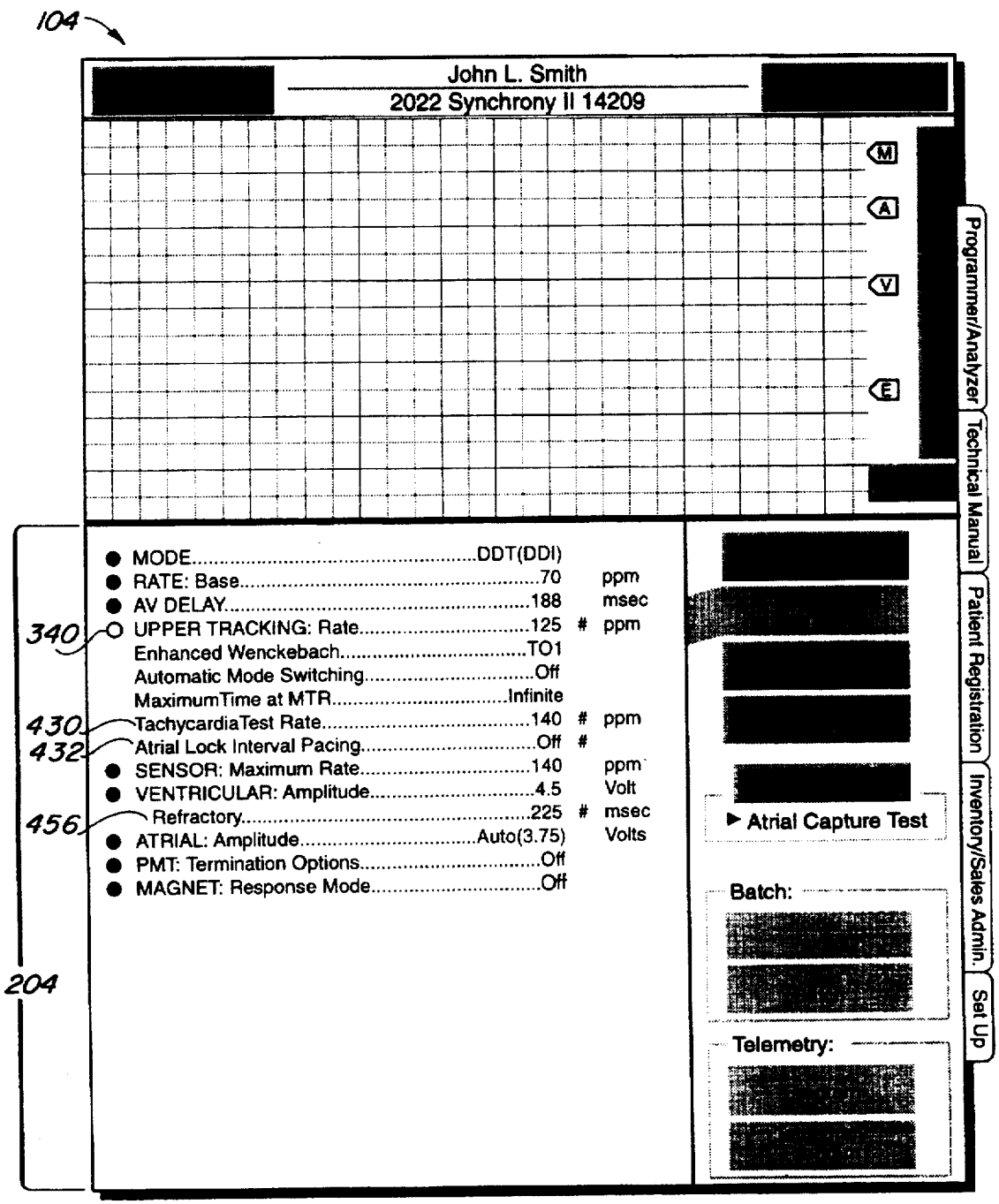
FIG. 13 is an illustrative screen display of the analyzer-programmer when the user has made the tachycardia test rate parameter and the atrial lock interval pacing parameter sticky in accordance with the present invention.

FIG. 13 shows the display screen 104 after the user has adjusted the upper tracking rate parameter 340, the tachycardia test rate parameter 430, and the atrial lock interval pacing parameter 432. The ventricular refractory parameter 456 remains changed as per FIG. 12. As compared to FIG. 12, the value of the upper tracking test rate parameter 340 has been changed from 165 pulses per minute to 125 pulses per minute, the value of the tachycardia test rate parameter 430 has been changed from 175 ppm to 140 ppm, the value of the atrial lock interval pacing parameter 432 has been changed from "On" to "Off," and the ventricular refractory parameter has been changed from 275 to 225. Adjustment of subordinate parameters 430 and 432 causes them to become sticky as preferably is indicated by a "#" mark. A "#" mark is also placed next to the upper tracking rate parameter 340 to remind the user that the value of the upper tracking rate parameter 340 has been adjusted, and a "#" mark remains next to the ventricular refractory parameter to indicate that it remains sticky.

Figure 14:
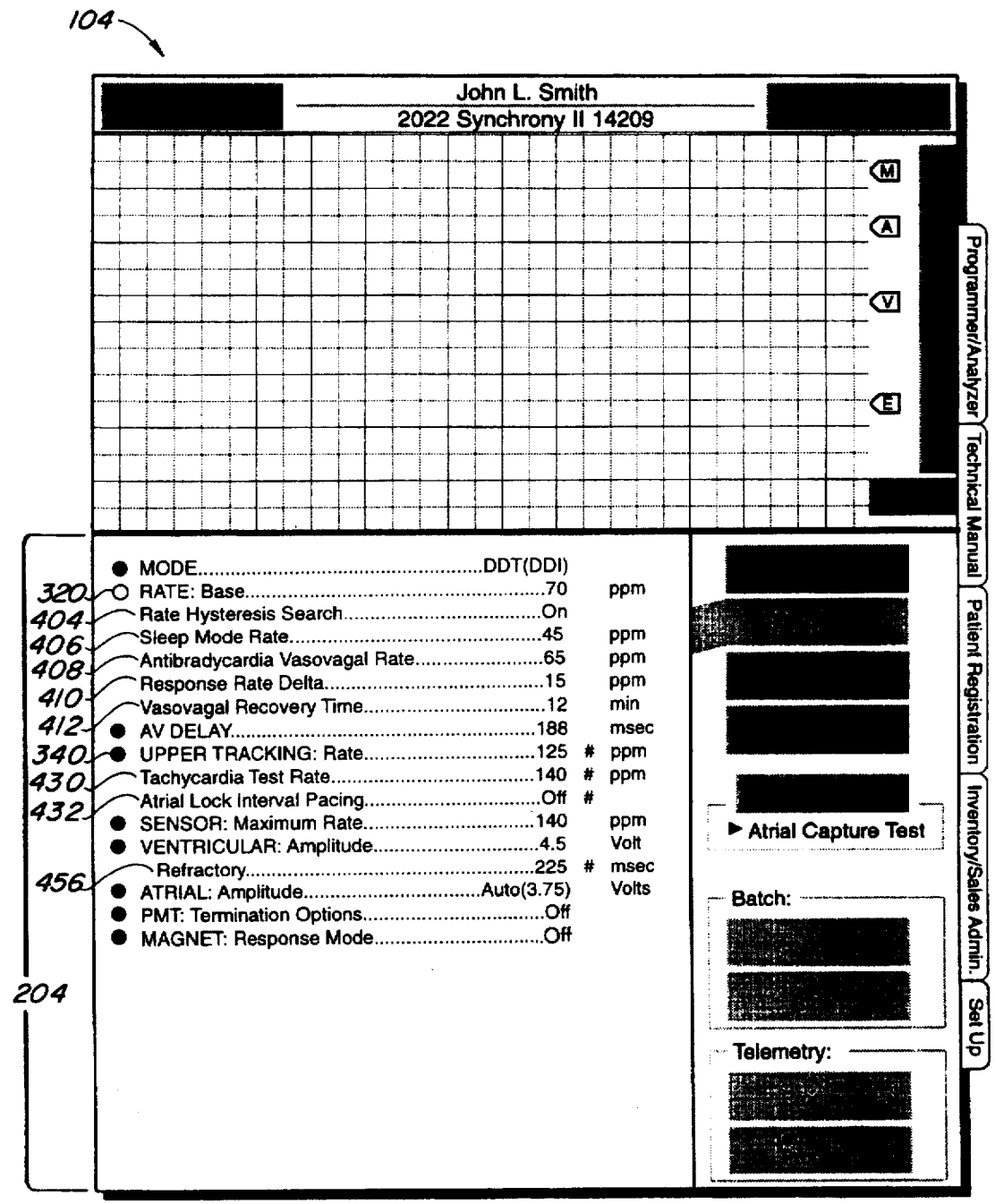
FIG. 14 is an illustrative screen display of the analyzer-programmer when the user has selected the base rate parameter, the screen display including the sticky parameters in accordance with the present invention.

FIG. 14 shows the display screen 104 when the user has selected the base rate parameter 320 for display after adjusting parameters 340, 430, 432, and 456. The subordinate parameters 430, 432, 456 which have been made sticky are displayed in addition to the subordinate parameters 404, 406, 408, 410, and 412 of the base rate parameter 320. By making the subordinate parameters 430, 432, and 456 sticky, the user is able to customize the display screen 104 to show the parameters that the user is interested in.

Preferably, the user also can make a parameter sticky by designating it as a sticky parameter, in addition to making a parameter sticky by adjusting its value.

In accordance with another aspect of the present invention, certain parameters preferably are linked. When a linked parameter is made sticky, all parameters linked to that parameter preferably are also made sticky. Linked parameters can include both subordinate parameters and key parameters. That is, subordinate parameters can be linked to other subordinate parameters only, or subordinate parameters can be linked to other subordinate parameters and key parameters.

An example of two parameters which preferably are linked are the ventricular blanking period and the atrial pulse amplitude. The ventricular blanking period parameter specifies a period of time, beginning after the application of an electrical impulse to the atrium, when the sensors located in the ventricle do not look for electrical signals from the heart. Providing a ventricular blanking period significantly reduces the possibility of the pacemaker mistaking an electrical pulse applied to the atrium by the pacemaker itself for an electrical signal generated by the heart.

The appropriate value of the ventricular blanking period is related the atrial amplitude. The atrial amplitude specifies the amplitude of the pulse applied to the atrium of the patient's heart. In general, an increase in the amplitude of the pulse applied to the atrium by the pacemaker requires an appropriate increase in the length of the ventricular blanking period.

Because the value of the ventricular blanking period depends in general on the amplitude of the pulse applied to the atrium, these two parameters are commonly adjusted together. In a preferred embodiment of the present invention shown in FIGS. 15 and 16, the atrial amplitude parameter 370 is linked to the ventricular blanking period parameter 458. (Note in FIGS. 15 and 16 that the mode parameter 310 has been set to DVI pacing, and that the use of inactive parameters as discussed below is shown.) This is an example of a key parameter, the atrial amplitude 370, being linked to a subordinate parameter, the ventricular blanking period parameter 458. Whenever, the user selects the atrial amplitude parameter 370 for adjustment, the ventricular blanking period parameter 458 preferably is displayed. Because the atrial amplitude parameter 370 is a key parameter, it preferably is displayed regardless of whether the ventricular blanking period parameter 458 has been selected.

Figure 15:
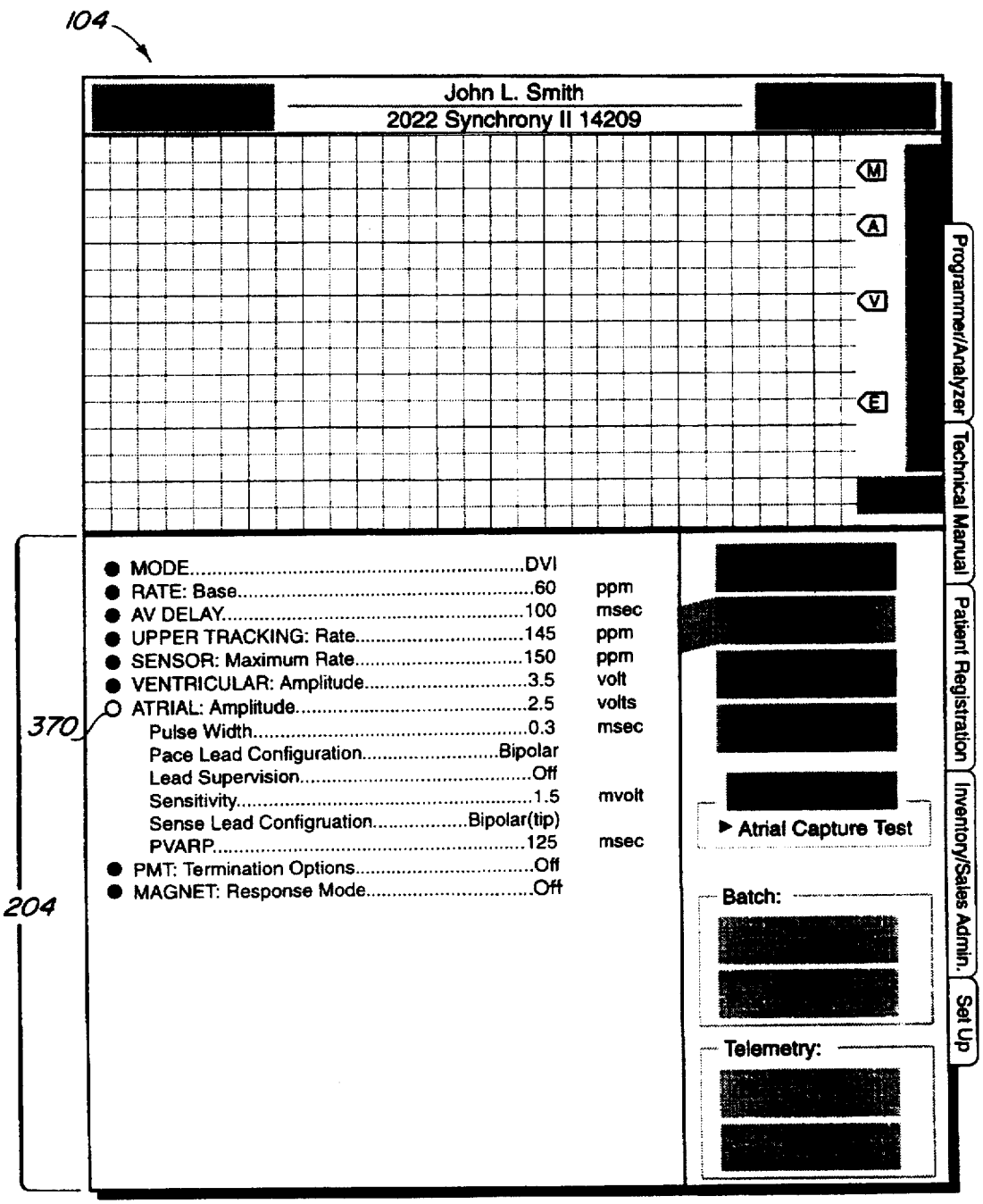
FIG. 15 is an illustrative screen display of the analyzer-programmer when the user has selected the atrial amplitude parameter in accordance with the present invention.
Figure 16:
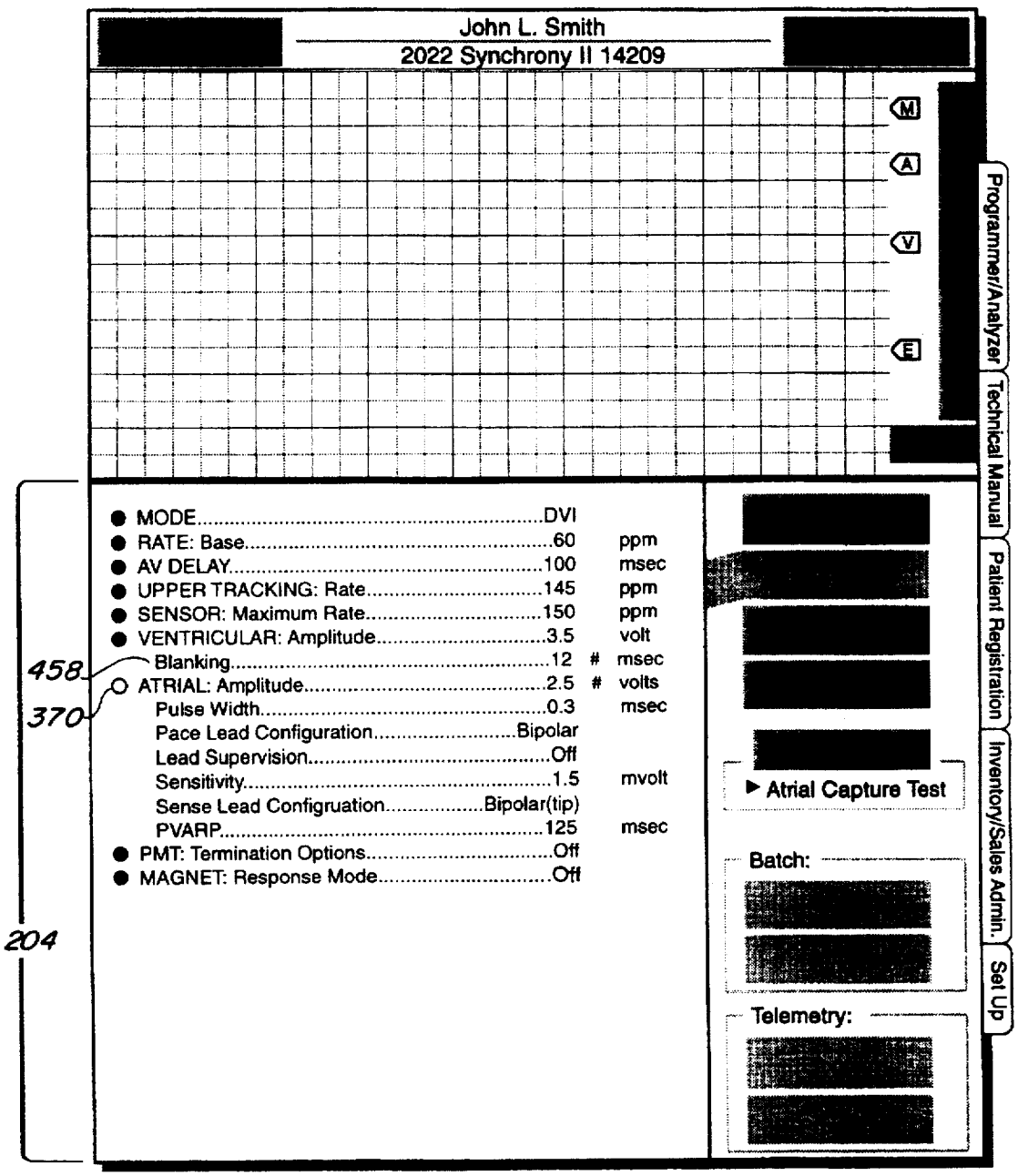
FIG. 16 is an illustrative screen display of the analyzer-programmer when the user has adjusted the value of the atrial amplitude parameter and caused a linked parameter to be displayed in accordance with the present invention.

FIG. 15 shows the display screen 104 when the user has selected the atrial amplitude parameter 370 for viewing, but before the user has selected it for adjustment. FIG. 16 shows the display screen 104 after the user has selected the atrial amplitude parameter 370 for adjustment. After the user selects the atrial amplitude parameter 370, the ventricular blanking period parameter 458 is made sticky because it is linked to the atrial amplitude parameter 370, and is thus displayed on the display screen 104. Both the ventricular blanking period parameter 458 and the atrial amplitude parameter 370 have "#" marks next to them indicating that they have been selected for adjustment.

Another example of parameters that preferably are linked are the base rate parameter 320, the ventricular refractory period parameter 456, the AV delay parameter 330, and the PVARP parameter 472. These parameters are commonly adjusted at the same time because the ventricular refractory period, the AV delay period, and PVARP must fit within a period of time determined by the base rate parameter 320. A higher base rate means that these parameters must occupy a shorter the period of time. Conversely a lower base rate permits relatively longer ventricular refractory, AV delay, and PVARP periods. Thus, a physician commonly must know the values of all four of these parameters when adjusting one or more of them.

In a preferred embodiment, the base rate parameter 320, the ventricular refractory period parameter 456, the AV delay parameter 330, and the PVARP parameter 472 are linked. This is an example of linking two key parameters and two subordinate parameters. When the user selects either key parameter for adjustment both subordinate parameters preferably are made sticky and displayed. When the user selects either of the subordinate parameters for adjustment, both subordinate parameters preferably are made sticky and displayed.

Figure 17:
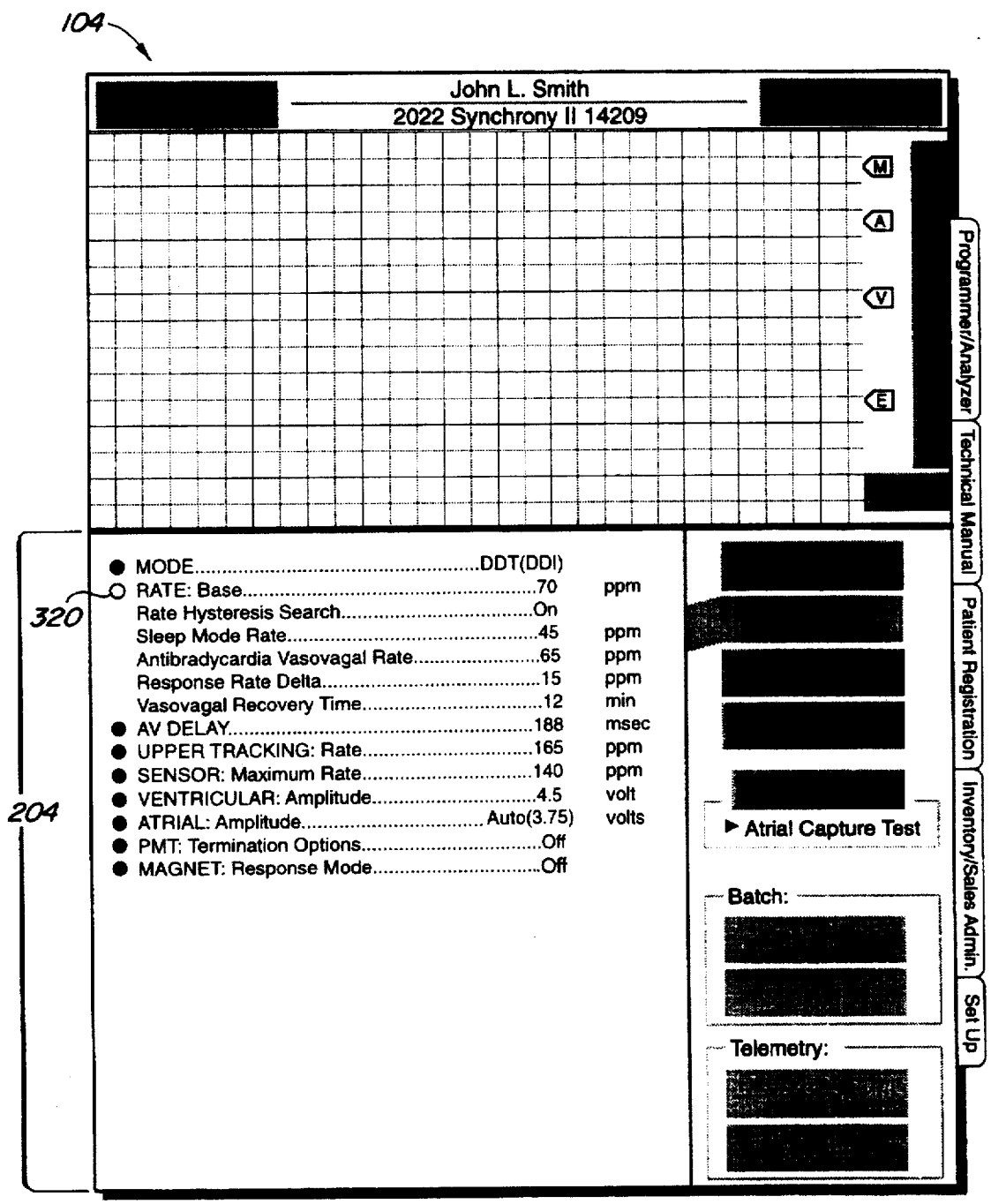
FIG. 17 is an illustrative screen display on the analyzer-programmer when the user has selected the base rate parameter in accordance with the present invention.

In FIG. 17, the user has selected the base rate parameter 320. FIG. 18 shows the display screen 104 after the user has adjusted the base rate parameter 320. The ventricular refractory period parameter 456 and the PVARP parameter 472 are displayed on the display screen 104 because they are linked to the base rate parameter 320.

As will be clear to those skilled in the art, other parameters can be linked in accordance with the present invention. Parameters which are typically adjusted at the same time preferably are linked together. In this manner, the user can conveniently determine the values of all the linked parameters and adjust them as necessary.

Preferably, the user is able to chose whether or not to display all linked parameters when any one of the parameters is chosen. This can be done, for example, by providing a button (not shown) on the display screen 104 which allows the physician to turn on or off the display of linked parameters. In a preferred embodiment, the linked parameters are pre-programmed into the tablet computer 100 and are not determined by the physician. In another embodiment, the user is able to designate which parameters are linked. It may be preferable to provide the linked parameters pre-programmed into the tablet computer so the physician is not burdened with the task of programming the linked parameters into the tablet computer.

In accordance with another aspect of the present invention, certain parameters preferably become inactive due to the value of certain other parameters. FIG. 19 shows the display screen 104 when the user has selected DVI as the status of the mode parameter 310. The DVI mode is a dual-chamber pacing mode in which pacing pulses are applied to both the atrium and the ventricle of the patient's heart. In the DVI mode, however, the pacemaker senses electrical signals only from the patient's ventricle. In contrast, in the DDI mode, the pacemaker senses electrical signals from both the atrium and the ventricle of the patient's heart.

When the user sets the mode parameter 310 to the DVI mode certain parameters relating to detecting electrical signals in the patient's atrium are no longer used. In accordance with the present invention, the atrial sensitivity parameter 468, the atrial sense lead configuration parameter 470, and the PVARP parameter 472, which relate to sensing signals from the atrium, are displayed as inactive when the user selects the DVI mode.

In a preferred embodiment, active parameters are displayed in the color black, while inactive parameters are displayed in the color grey. In FIG. 19, parameters 468, 470, and 472 are displayed in the color grey, indicating that they are inactive. As will be clear to those skilled in the art, other indicia can be used to designate inactive parameters in accordance with the present invention.

The processing and memory circuit 142 and the display logic and memory circuit 144 of the tablet computer 100 preferably are programmed to display the programmable parameters in accordance with the present invention. It will be clear to those skilled in the art that the tablet computer 100 can be programmed to display program parameters in accordance with the present invention using known programming techniques.

Figure 20:
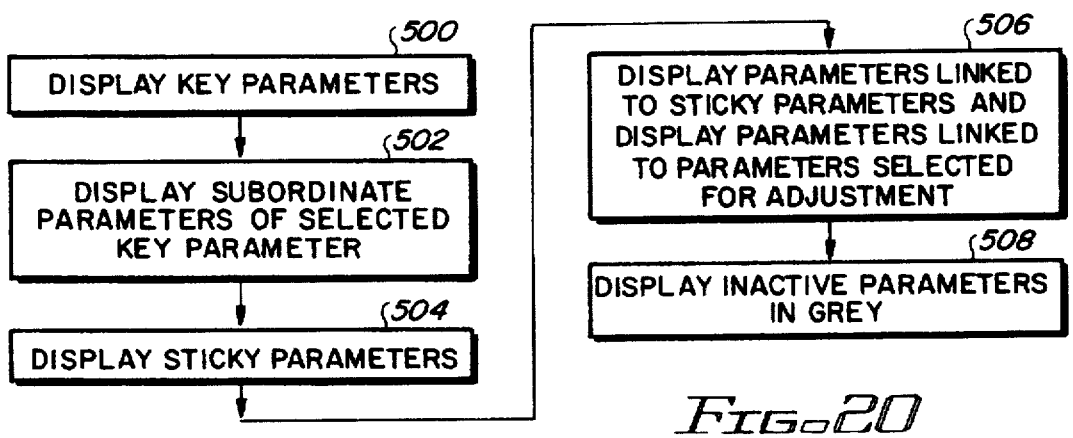
FIG. 20 is a flowchart of the steps carried out by the tablet computer of FIG. 1 in accordance with the present invention.

FIG. 20 shows a flowchart of the steps preferably carried out by the tablet computer 100 in accordance with a preferred embodiment of the present invention. In step 500, the key parameters are displayed on the display screen 104. In step 502, the subordinate parameters of the selected key parameter are displayed on the display screen 104, while in step 504 sticky parameters are displayed. In step 506, parameters linked to sticky parameters and parameters linked to parameters selected for adjustment are displayed. Finally, in step 508 inactive parameters are displayed in grey.

Thus a method and system are provided for organizing, viewing and manipulating information in an implantable device programmer. One skilled in the art will appreciate that the present invention can be practiced by other than the described embodiments, which are presented for purposes of illustration and not of limitation, and the present invention is limited only by the claims which follow.

What is claimed is:

1. A method of displaying programming information relating to an implantable cardiac stimulating device on a display screen of an analyzer-programmer which communicates with the implantable cardiac stimulating device, and which has an input device for allowing a user to input information into the analyzer-programmer comprising the steps of:

providing a set of programmable parameters relating to the implantable cardiac stimulating device;

providing key parameters from the set of programmable parameters;

providing associated subordinate parameters for each of the key parameters from the set of programmable parameters;

displaying on the display screen a graphical representation of the key parameters;

allowing the user to select a first one of the key parameters for display using the input device;

displaying on the display screen a graphical representation of the associated subordinate parameters of the first selected key parameter;

allowing the user to select a second one of the key parameters for display using the input device; and displaying on the display screen a graphical representation of the associated subordinate parameters of the second selected key parameter.

2. The method of claim 1, further comprising, after the step of displaying on the display screen a graphical representation of the associated subordinate parameters of the first selected key parameter, and before the step of allowing the user to select a second one of the key parameters for display using the input device, the step of:

allowing the user to select a first one of the associated subordinate parameters of the first selected key parameter using the input device; and wherein the step of displaying on the display screen a graphical representation of the associated subordinate parameters of the second selected key parameter further comprises:

displaying on the display screen the first selected subordinate parameter of the first selected key parameter, and not displaying on the display screen the associated subordinate parameters of the first selected key parameter which were not selected by the user.

3. The method of claim 2, further comprising, after the step of displaying on the display screen a graphical representation of the associated subordinate parameters of the second selected key parameter, the steps of:

allowing the user to select a first one of the associated subordinate parameters of the second selected key parameter using the input device;

allowing the user to select a third one the key parameters using the input device;

displaying on the display screen a graphical representation of the associated subordinate parameters of the third selected key parameter; and displaying on the display screen the first selected subordinate parameter of the second selected key parameter, and not displaying on the display screen the associated subordinate parameters of the second selected key parameter which were not selected by the user.

4. The method of claim 1, further comprising, after the step of displaying on the display screen a graphical representation of the associated subordinate parameters of the first selected key parameter, and before the step of allowing the user to select a second one of the key parameters for display using the input device, the step of:

allowing the user to select first and second associated subordinate parameters of the first selected key parameter using the input device; and wherein the step of displaying on the display screen a graphical representation of the associated subordinate parameters of the second selected key parameter further comprises:

displaying on the display screen the first and second selected subordinate parameters of the first selected key parameter, and not displaying on the display screen the associated subordinate parameters of the first selected key parameter which were not selected by the user.

5. A method of displaying programming information relating to an implantable cardiac stimulating device on a display screen of an analyzer-programmer which communicates with the implantable cardiac stimulating device, and which has an input device for allowing a user to input information into the analyzer-programmer comprising the steps of:

providing a set of programmable parameters relating to the implantable cardiac stimulating device;

providing key parameters from the set of programmable parameters;

providing associated subordinate parameters for each of the key parameters from the set of programmable parameters;

providing a plurality of linked parameters from the set of programmable parameters;

displaying on the display screen a graphical representation of the key parameters;

allowing the user to select one of the key parameters for display using the input device;

displaying on the display screen a graphical representation of the associated subordinate parameters of the selected key parameter, the displayed key parameters and the displayed associated subordinate parameters of the selected including key parameter including at least one of the plurality of linked parameters;

allowing the user to select using the input device one of the at least one of the plurality of linked parameters which is displayed; and displaying on the display screen a graphical representation of the plurality of linked parameters after the user has selected the one of the at least one of the plurality of linked parameters.

6. The method of claim 5, wherein the plurality of linked parameters comprises a first one of the key parameters and at least one of said associated subordinate parameters; and wherein the step of allowing the user to select using the input device one of the at least one of the plurality of linked parameters which is displayed comprises allowing the user to select using the input device the first key parameter.

7. The method of claim 5, wherein the step of providing a plurality of linked parameters from the set of programmable parameters comprises providing a plurality of linked associated subordinate parameters.

8. The method of claim 5, wherein the step of providing a plurality of linked parameters from the set of programmable parameters comprises providing at least one linked key parameter and at least one linked associated subordinate parameter.

9. A method of displaying programming information relating to an implantable cardiac stimulating device on a display screen of an analyzer-programmer which communicates with the implantable cardiac stimulating device, and which has an input device for allowing a user to input information into the analyzer-programmer comprising the steps of:

providing a set of programmable parameters relating to the implantable cardiac stimulating device, each of the programmable parameters having a value;

providing key parameters from the set of programmable parameters;

providing associated subordinate parameters for each of the key parameters from the set of programmable parameters;

displaying on the display screen a graphical representation of the key parameters;

displaying on the display screen the value of each of the key parameters;

allowing the user to select one of the key parameters for display using the input device;

displaying on the display screen a graphical representation of the associated subordinate parameters of the selected key parameter;

displaying on the display screen the value of each of the associated subordinate parameters of the selected key parameter;

allowing the user to adjust the value of one of the displayed programmable parameters to a predetermined value using the input device; and displaying on the display screen at least one programmable parameter as inactive when the user adjusts the value of one of the displayed programmable parameters to the predetermined value.

10. An analyzer-programmer for use with an implantable cardiac stimulating device, said analyzer-programmer comprising:

a display means for displaying information relating to said implantable cardiac stimulating device;

a memory means;

an input means;

a processor means which communicates with each of said display means, said memory means, and said input means; wherein said processing means controls said display means, said memory means, and said input means such that:

a graphical representation of key parameters chosen from a set of programmable parameters relating to said implantable cardiac stimulating device is displayed on said display means;

when the user selects a first one of said key parameters using said input means, a graphical representation of subordinate parameters associated with said first selected key parameter is displayed on said display means; and when the user selects a second one of said key parameters using said input means, a graphical representation of subordinate parameters associated with said second selected key parameter is displayed on said display means.

11. The analyzer-programmer of claim 10 further comprising:

means for selecting a first one of said subordinate parameters associated with said first selected key parameter using said input means before selecting said second one of said key parameters, thereby designating a first selected subordinate parameter associated with said first selected key parameter and designating at least one non-selected subordinate parameter associated with said first selected key parameter which has not been selected; and means for displaying a graphical representation of said first selected subordinate parameter associated with said first selected key parameter and not displaying said at least one non-selected subordinate parameter associated with said first selected key parameter on said display means when the user selects said second one of said key parameters.

12. The analyzer-programmer of claim 11 further comprising:

means for selecting a first one of said subordinate parameters associated with said second selected key parameter using said input means, thereby designating a first selected subordinate parameter associated with said second selected key parameter and designating at least one non-selected subordinate parameter associated with said second selected key parameter which has not been selected;

means for selecting a third one of said key parameters via said input means, thereby designating a third selected key parameter and displaying a graphical representation of subordinate parameters associated with said third selected key parameter on said display means; and means for displaying a graphical representation of said first selected subordinate parameter associated with said second selected key parameter and not displaying said at least one non-selected subordinate parameter associated with said second selected key parameter on said display means.

13. The analyzer-programmer of claim 10 further comprising:

means for selecting a first and a second of said subordinate parameters associated with said first selected key parameter via said input means, thereby designating first and second selected subordinate parameters associated with said first selected key parameter and thereby designating at least one non-selected subordinate parameter associated with said first selected key parameter which has not been selected; and means for displaying graphical representations of said first and second selected subordinate parameters associated with said first selected key parameter and not displaying said at least one non-selected subordinate parameter associated with said first selected key parameter on said display means.

14. An analyzer-programmer for use with an implantable cardiac stimulating device, said analyzer-programmer comprising:

a display means for displaying information relating to said implantable cardiac stimulating device;

a memory means;

an input means;

a processor means which communicates with each of said display means, said memory means, and said input means; wherein said processing means controls said display means, said memory means, and said input means such that:

a graphical representation of key parameters chosen from a set of programmable parameters relating to said implantable cardiac stimulating device is displayed on said display means;

when the user selects a first one of said key parameters using said input means, a graphical representation of subordinate parameters associated with said first selected key parameter is displayed on said display means, said key parameters and said subordinate parameters associated with said first selected key parameter including at least one of a plurality of linked parameters chosen from said set of programmable parameters; and when the user selects one of said at least one of said plurality of linked parameters which is displayed on said display means, a graphical representation of said plurality of linked parameters is displayed on said display means.

15. The analyzer-programmer of claim 14, wherein said plurality of linked parameters comprises at least one of said key parameters.

16. The analyzer-programmer of claim 15, wherein said plurality of linked parameters comprises at least one of said subordinate parameters.

17. An analyzer-programmer for use with an implantable cardiac stimulating device, said analyzer-programmer comprising:
- a display means for displaying information relating to said implantable cardiac stimulating device;
- a memory means;
- an input means;
- a processor means which communicates with each of said display means, said memory means, and said input means; wherein said processor means controls said display means, said memory means, and said input means such that:
  - a graphical representation of key parameters chosen from a set of programmable parameters relating to said implantable cardiac stimulating device is displayed on said display means;
  - a graphical representation of a value of each of said key parameters is displayed on said display means;
  - when the user selects a first one of said key parameters using said input means, a graphical representation of subordinate parameters associated with said first selected key parameter is displayed on said display means, and a graphical representation of a value of each of said subordinate parameter associated with said first selected key parameter is displayed on said display means; and
  - when the user adjusts to a predetermined value said value of one of said programmable parameters which is displayed on said display means, a graphical representation of an inactive parameter is displayed on said display means.

18. For use with an analyzer-programmer having a display means, a memory means, a processor means, and an input means, said processor means communicating with said memory means and said display means, said input means for allowing a user to input information into said analyzer-programmer, said analyzer-programmer communicating with an implantable cardiac stimulating device, a method of operating said analyzer-programmer in order to display information to the user comprising the steps of:
- providing a set of programmable parameters relating to said implantable cardiac stimulating device;
- providing key parameters from said set of programmable parameters;
- providing associated subordinate parameters for each of said key parameters from said set of programmable parameters;
- displaying on said display means a graphical representation of said key parameters;
- allowing the user to select a first one of said key parameters via said input means, the user thereby designating a first selected key parameter;
- displaying on said display means said subordinate parameters associated with said first selected key parameter;
- allowing the user to select a second one of said key parameters via said input means, the user thereby designating a second selected key parameter; and
- displaying on said display means said subordinate parameters associated with said second selected key parameter.

19. The method of claim 18, further comprising, after said step of displaying on said display means said subordinate parameters associated with said first selected key parameters, and before said step of allowing the user to select a second one of said key parameters via said input means, the step of:
- allowing the user to select a first one of said subordinate parameters associated with said first selected key parameter via said input means, the user thereby designating a first selected subordinate parameter associated with said first selected key parameter and the user thereby designating at least one non-selected subordinate parameter associated with said first selected key parameter which has not been selected by the user; and
- wherein said step of displaying on said display means said subordinate parameters associated with said second selected key parameter further comprises:
  - displaying on said display means said first selected subordinate parameter associated with said first selected key parameter, and not displaying on said display means said at least one non-selected subordinate parameter associated with said first selected key parameter.

20. The method of claim 19, further comprising, after said step of displaying on said display means said subordinate parameters associated with said second selected key parameter, the steps of:
- allowing the user to select a first one of said subordinate parameters associated with said second selected key parameter via said input means, the user thereby designating a first selected subordinate parameter associated with said second selected key parameter and the user thereby designating at least one non-selected subordinate parameter associated with said second selected key parameter which has not been selected by the user;
- allowing the user to select a third one of said key parameters via said input means, the user thereby designating a third selected key parameter;
- displaying on said display means said subordinate parameters associated with said third selected key parameter; and
- displaying on said display means said first selected subordinate parameter associated with said second selected key parameter, and not displaying on said display means said at least one non-selected subordinate parameter associated with said second selected key parameter.

21. The method of claim 18, further comprising, after said step of displaying on said display means said subordinate parameters associated with said first selected key parameters, and before said step of allowing the user to select a second one of said key parameters via said input means, the step of:
- allowing the user to select a first and a second of said subordinate parameters associated with said first selected key parameter via said input means, the user thereby designating first and second selected subordinate parameters associated with said first selected key parameter and the user thereby designating at least one non-selected subordinate parameter associated with said first selected key parameter which has not been selected by the user; and wherein said step of displaying on said display means said subordinate parameters associated with said second selected key parameter further comprises:
  - displaying on said display means said first and second selected subordinate parameters associated with said first selected key parameter, and not displaying on said display means said at least one non-selected subordinate parameter associated with said first selected key parameter.

22. For use with an analyzer-programmer having a display screen, a memory device, a processor circuit, and an input device, said processor circuit communicating with said memory device and said display screen, said input device for allowing a user to input information into said analyzer-programmer, said analyzer-programmer communicating with an implantable cardiac stimulating device, a method of operating said analyzer-programmer in order to display information to the user comprising the steps of:

providing a set of programmable parameters relating to said implantable cardiac stimulating device;

providing key parameters from said set of programmable parameters;

providing associated subordinate parameters for each of said key parameters from said set of programmable parameters;

providing a plurality of linked parameters from said set of programmable parameters;

displaying on said display screen a graphical representation of said key parameters;

allowing the user to select a first one of said key parameters via said input device, the user thereby designating a first selected key parameter;

displaying on said display screen said subordinate parameters associated with said first selected key parameter, said key parameters and said subordinate parameters associated with said first selected key parameter including at least one of said plurality of linked parameters;

allowing the user to select via said input device one of said at least one of said plurality of linked parameters which is displayed on said display screen; and displaying on said display screen a graphical representation of said plurality of linked parameters after the user has selected said one of said at least one of the plurality of linked parameters.

23. The analyzer-programmer of claim 22, wherein the step of providing said plurality of linked parameters from said set of programmable parameters further comprises the step of providing a plurality of linked associated subordinate parameters from said set of programmable parameters.

24. The analyzer-programmer of claim 22, wherein the step of providing said plurality of linked parameters from said set of programmable parameters further comprises the step of at least one linked key parameter and at least one linked associated subordinate parameter from said set of programmable parameters.

25. For use with an analyzer-programmer having a display screen, a memory device, a processor circuit, and an input device, said processor circuit communicating with said memory device and said display screen, said input device for allowing a user to input information into said analyzer-programmer, said analyzer-programmer communicating with an implantable cardiac stimulating device, a method of operating said analyzer-programmer in order to display information to the user comprising the steps of:

providing a set of programmable parameters relating to said implantable cardiac stimulating device, each of said programmable parameters having a value;

providing key parameters from said set of programmable parameters;

providing associated subordinate parameters for each of said key parameters from said set of programmable parameters;

displaying on said display screen a graphical representation of said key parameters;

displaying on said display screen a graphical representation of said values of said key parameters;

allowing the user to select a first one of said key parameters via said input device, the user thereby designating a first selected key parameter;

displaying on said display screen said subordinate parameters associated with said first selected key parameter;

displaying on said display screen said values of said subordinate parameters associated with said first selected key parameter;

allowing the user to adjust to a predetermined value said value of one of either said key parameters or said subordinate parameters associated with said first selected key parameter; and displaying on said display screen at least one programmable parameter as inactive when the user adjusts to said predetermined value said value of one of either said key parameters or said subordinate parameters associated with said first selected key parameter.

\* \* \* \* \*